United States Patent
Greiner-Stoeffele et al.

(10) Patent No.: US 9,796,994 B2
(45) Date of Patent: Oct. 24, 2017

(54) METHOD FOR PRODUCING SERRATIA MARCESCENS NUCLEASE USING A BACILLUS EXPRESSION HOST

(75) Inventors: Thomas Greiner-Stoeffele, Leipzig (DE); Stefan Schoenert, Leipzig (DE)

(73) Assignee: c-LEcta GmbH, Leipzig (DE)

( * ) Notice: Subject to any disclaimer, the term of this patent is extended or adjusted under 35 U.S.C. 154(b) by 0 days.

(21) Appl. No.: 13/364,889

(22) Filed: Feb. 2, 2012

(65) Prior Publication Data

US 2012/0135498 A1    May 31, 2012

Related U.S. Application Data

(63) Continuation of application No. PCT/EP2010/004709, filed on Aug. 2, 2010.

(30) Foreign Application Priority Data

Aug. 3, 2009 (EP) .................................. 09009992

(51) Int. Cl.
*C12N 9/22* (2006.01)
*C12P 21/02* (2006.01)

(52) U.S. Cl.
CPC ............... *C12P 21/02* (2013.01); *C12N 9/22* (2013.01); *C07K 2319/036* (2013.01); *C07K 2319/21* (2013.01); *C07K 2319/22* (2013.01); *C07K 2319/24* (2013.01)

(58) Field of Classification Search
CPC ..... C12N 1/20; C12N 9/22; C12Y 301/30002
USPC .......................................... 435/196, 252.31
See application file for complete search history.

(56) References Cited

U.S. PATENT DOCUMENTS

| | | | | |
|---|---|---|---|---|
| 5,173,418 A * | 12/1992 | Molin et al. | .................. | 435/198 |
| 5,821,088 A * | 10/1998 | Darzins et al. | .............. | 435/69.7 |
| 6,617,148 B2 * | 9/2003 | Bedzyk | .................. | C12N 15/75 435/243 |
| 2005/0214922 A1 * | 9/2005 | Okuda | ..................... | C12N 9/54 435/226 |
| 2007/0281342 A1 | 12/2007 | DeAngelis | | |

FOREIGN PATENT DOCUMENTS

| | | |
|---|---|---|
| EP | 0229866 B1 | 12/1992 |
| WO | WO 99/04019 A1 | 1/1999 |
| WO | WO 00/39323 A2 | 7/2000 |
| WO | WO 2004/060909 A2 | 7/2004 |

OTHER PUBLICATIONS

Biosaxony, "Serratia Nuclease from C-Lecta—Innovative Production of a Key Enzyme", Jul. 7, 2010, 1 page.*
Phan et al., Prot. Express. Purif. 46:189-195, 2006.*
Ming-Ming et al., Biotechnol. Lett. 28:1713-1718, 2006.*
Ford et al., Prot. Express. Purif. 2:95-107, 1991.*
"Serratia nuclease of c LEcta—innovative production of a key enzyme", Press release by c-Lecta, Jul. 6, 2010, 2 pages.*
Ahrenholtz et al., "A Conditional Suicide System in *Escherichia coli* Based on the Intracellular Degradation of DNA", Appl. Environmen. Microbiol. 60:3746-3751, 1994.*
Jin et al., J. Mol. Biol. 256:264-278, 1996.*
Ohmura et al., J. Biochem. 95:87-93, 1984.*
Olempska-Beer et al., Regul. Toxicol. Pharmacol. 45:144-158, 2006.*
Viegas et al., Plasmid 51:256-264, 2004.*
Yamamoto et al., J. Bacteriol. 183:5110-5121, 2001.*
English Translation of International Preliminary Report on Patentability dated Feb. 7, 2012 (nine (9) pages).
Kirsten Biedermann et al., "Fermentation Studies of the Secretion of Serratia Marcescens Nuclease by *Escherichia coli*", Applied and Environmental Microbiology, Jun. 1990, vol. 56, No. 6, pp. 1833-1838, American Society for Microbiology, XP-002561838.
Y. Dieye et al., "Design of a Protein-Targeting System for Lactic Acid Bacteria", Journal of Bacteriology, Jul. 2001, vol. 183, No. 14, pp. 4157-4166, American Society for Microbiology, XP-002561839.
Steven Kovacevic et al., "Secretion of Staphylococcal Nuclease by Bacillus Subtilis", Journal of Bacteriology, May 1985, vol. 162, No. 2, pp. 521-528, American Society for Microbiology, XP-002601752.
Kay Terpe, "Overview of Bacterial Expression Systems for Heterologous Protein Production: from Molecular and Biochemical Fundamentals to Commerical Systems", Applied Microbial Biotechnol. (2006), No. 72, pp. 211-222, Springer.
Anderson Miyoshi et al., "A Xylose-Inducible Expression System for Lactococcus Lactis", FEMS Microbiology Letters 239, (2004), pp. 205-212, Elsevier.
European Search Report with English Translation dated Jan. 5, 2010 (six (6) pages).
Form PCT/ISA/237 (six (6) pages), Jan. 2010.
International Search Report with English Translation dated Oct. 6, 2010 (six (6) pages).
Altschul, et al., "Gapped BLAST and PSI-BLAST: a new generation of protein database search programs," Nucleic Acids Research, 1997, vol. 25, No. 17, pp. 3389-3402.
Nakamura, et al., "Gene cloning and characterization of a novel extracellular ribonuclease of *Bacillus subtilis*," Eur. J. Biochem, 1992, vol. 209, pp. 121-127.

* cited by examiner

*Primary Examiner* — David J Steadman
(74) *Attorney, Agent, or Firm* — Agris & Von Natzmer, LLP; Joyce Von Natzmer

(57) ABSTRACT

A method for producing a nuclease of a gram negative bacterium or a nuclease preparation containing a nuclease of a gram negative bacterium including expression of the nuclease in a gram positive bacterium and subsequent secretion of the nuclease, as well as a nuclease or a nuclease preparation that can be obtained by this method.

24 Claims, No Drawings

SEQUENCE LISTING

<160> NUMBER OF SEQ ID NOS: 187

<210> SEQ ID NO 1
<211> LENGTH: 801
<212> TYPE: DNA
<213> ORGANISM: Serratia marcescens

<400> SEQUENCE: 1

```
atgcgcttta acaacaagat gttggccttg ccgccctgc tgttcgccgc gcaggcgtcg      60
gccgacacgc tcgaatccat cgacaactgc gcggtcggct ccccgaccgg cggcagcagc     120
aacgtgtcta tcgtgcgcca tgcttatacg ttgaacaaca acagcaccac caagttcgcc    180
aactgggtgg cctatcacat caccaaagac acgccggcca gcgcaagac gcgcaactgg     240
aaaaccgatc cggctctcaa tccggcggac actctggcgc cgccgattta caccggtgcc    300
aacgccgcgc tgaaggtcga tcgcggtcat caggcgccgc tggcctcgct ggcgggcgtt    360
tccgactggg aatcgttgaa ctacctgtcc aacatcacgc cgcaaaagtc cgatctgaac    420
cagggcgcct gggctcggct ggaagatcag gaacgcaagc tgatcgatcg cgccgatatc    480
tcctcggtct ataccgtgac cgggccgctg tatgagcgcg atatgggcaa actgccgggc    540
acccagaaag cgcacaccat ccccagcgcc tactggaagg taattttcat caacaacagc    600
ccggcggtga accactatgc cgccttcctg ttcgaccaga acacgccgaa gggcgccgat    660
ttctgccaat tccgcgtgac ggtggacgag atcgagaaac gcaccggcct gatcatctgg    720
gccggtctgc cggacgacgt gcaggcttcg ctgaagagca aaccgggcgt tctgccggag    780
ttgatgggct gcaaaaactg a                                              801
```

<210> SEQ ID NO 2
<211> LENGTH: 21
<212> TYPE: PRT
<213> ORGANISM: Serratia marcescens

<400> SEQUENCE: 2

Met Arg Phe Asn Asn Lys Met Leu Ala Leu Ala Ala Leu Leu Phe Ala
1               5                   10                  15

Ala Gln Ala Ser Ala
            20

<210> SEQ ID NO 3
<211> LENGTH: 245
<212> TYPE: PRT
<213> ORGANISM: Serratia marcescens

<400> SEQUENCE: 3

Asp Thr Leu Glu Ser Ile Asp Asn Cys Ala Val Gly Cys Pro Thr Gly
1               5                   10                  15

Gly Ser Ser Asn Val Ser Ile Val Arg His Ala Tyr Thr Leu Asn Asn
            20                  25                  30

Asn Ser Thr Thr Lys Phe Ala Asn Trp Val Ala Tyr His Ile Thr Lys

```
                   35                   40                  45
Asp Thr Pro Ala Ser Gly Lys Thr Arg Asn Trp Lys Thr Asp Pro Ala
 50                  55                  60

Leu Asn Pro Ala Asp Thr Leu Ala Pro Ala Asp Tyr Thr Gly Ala Asn
 65                  70                  75                  80

Ala Ala Leu Lys Val Asp Arg Gly His Gln Ala Pro Leu Ala Ser Leu
                 85                  90                  95

Ala Gly Val Ser Asp Trp Glu Ser Leu Asn Tyr Leu Ser Asn Ile Thr
                100                 105                 110

Pro Gln Lys Ser Asp Leu Asn Gln Gly Ala Trp Ala Arg Leu Glu Asp
                115                 120                 125

Gln Glu Arg Lys Leu Ile Asp Arg Ala Asp Ile Ser Ser Val Tyr Thr
130                 135                 140

Val Thr Gly Pro Leu Tyr Glu Arg Asp Met Gly Lys Leu Pro Gly Thr
145                 150                 155                 160

Gln Lys Ala His Thr Ile Pro Ser Ala Tyr Trp Lys Val Ile Phe Ile
                165                 170                 175

Asn Asn Ser Pro Ala Val Asn His Tyr Ala Ala Phe Leu Phe Asp Gln
                180                 185                 190

Asn Thr Pro Lys Gly Ala Asp Phe Cys Gln Phe Arg Val Thr Val Asp
                195                 200                 205

Glu Ile Glu Lys Arg Thr Gly Leu Ile Ile Trp Ala Gly Leu Pro Asp
210                 215                 220

Asp Val Gln Ala Ser Leu Lys Ser Lys Pro Gly Val Leu Pro Glu Leu
225                 230                 235                 240

Met Gly Cys Lys Asn
                245

<210> SEQ ID NO 4
<211> LENGTH: 32
<212> TYPE: PRT
<213> ORGANISM: Bacillus subtilis

<400> SEQUENCE: 4

Met Lys Lys Lys Lys Thr Trp Lys Arg Phe Leu His Phe Ser Ser Ala
 1               5                  10                  15

Ala Leu Ala Ala Gly Leu Ile Phe Thr Ser Ala Ala Pro Ala Glu Ala
                20                  25                  30

<210> SEQ ID NO 5
<211> LENGTH: 33
<212> TYPE: PRT
<213> ORGANISM: Bacillus subtilis

<400> SEQUENCE: 5

Met Phe Ala Lys Arg Phe Lys Thr Ser Leu Leu Pro Leu Phe Ala Gly
 1               5                  10                  15

Phe Leu Leu Leu Phe His Leu Val Leu Ala Gly Pro Ala Ala Ala Ser
                20                  25                  30

Ala

<210> SEQ ID NO 6
<211> LENGTH: 29
<212> TYPE: PRT
<213> ORGANISM: Artificial
<220> FEATURE:
<223> OTHER INFORMATION: Kuenstliche Sekretionssequenz
```

-continued

```
<400> SEQUENCE: 6

Met Arg Ser Lys Lys Leu Trp Ile Ser Leu Leu Phe Ala Leu Thr Leu
1               5                   10                  15

Ile Phe Thr Met Ala Phe Ser Asn Met Ser Val Gln Ala
            20                  25

<210> SEQ ID NO 7
<211> LENGTH: 22
<212> TYPE: PRT
<213> ORGANISM: Artificial
<220> FEATURE:
<223> OTHER INFORMATION: kuenstliche Sekretionssequenz

<400> SEQUENCE: 7

Met Lys Leu Ala Lys Arg Val Ser Ala Leu Thr Pro Ser Thr Thr Leu
1               5                   10                  15

Ala Ile Thr Ala Lys Ala
            20

<210> SEQ ID NO 8
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 8

Met Pro Tyr Leu Lys Arg Val Leu Leu Leu Val Thr Gly Leu Phe
1               5                   10                  15

Met Ser Leu Phe Ala Val Thr Ala Thr Ala Ser Ala
            20                  25

<210> SEQ ID NO 9
<211> LENGTH: 38
<212> TYPE: PRT
<213> ORGANISM: Artificial
<220> FEATURE:
<223> OTHER INFORMATION: kuenstliche Sekretionssequenz

<400> SEQUENCE: 9

Met Met Arg Arg Arg Lys Arg Ser Asp Met Lys Arg Ser Ile Ser Ile
1               5                   10                  15

Phe Ile Thr Cys Leu Leu Ile Thr Leu Leu Thr Met Gly Gly Met Ile
            20                  25                  30

Ala Ser Pro Ala Ser Ala
        35

<210> SEQ ID NO 10
<211> LENGTH: 30
<212> TYPE: PRT
<213> ORGANISM: Artificial
<220> FEATURE:
<223> OTHER INFORMATION: kuenstliche Sekretionssequenz

<400> SEQUENCE: 10

Met Arg Lys Lys Thr Lys Asn Arg Leu Ile Ser Ser Val Leu Ser Thr
1               5                   10                  15

Val Val Ile Ser Ser Leu Leu Phe Pro Gly Ala Ala Gly Ala
            20                  25                  30

<210> SEQ ID NO 11
<211> LENGTH: 27
<212> TYPE: PRT
```

```
<213> ORGANISM: Artificial
<220> FEATURE:
<223> OTHER INFORMATION: kuenstliche Sekretionssequenz

<400> SEQUENCE: 11

Met Lys Trp Asn Pro Leu Ile Pro Phe Leu Leu Ile Ala Val Leu Gly
1               5                   10                  15

Ile Gly Leu Thr Phe Phe Leu Ser Val Lys Gly
            20                  25

<210> SEQ ID NO 12
<211> LENGTH: 32
<212> TYPE: PRT
<213> ORGANISM: Artificial
<220> FEATURE:
<223> OTHER INFORMATION: kuenstliche Sekretionssequenz

<400> SEQUENCE: 12

Met Gly Asn Thr Arg Lys Lys Val Ser Val Ile Gly Ala Gly Phe Thr
1               5                   10                  15

Gly Ala Thr Thr Ala Phe Leu Ile Ala Gln Lys Glu Leu Ala Asp Val
            20                  25                  30

<210> SEQ ID NO 13
<211> LENGTH: 37
<212> TYPE: PRT
<213> ORGANISM: Artificial
<220> FEATURE:
<223> OTHER INFORMATION: kuenstliche Sekretionssequenz

<400> SEQUENCE: 13

Met Lys Asn Arg Leu Phe Ile Leu Ile Cys Phe Cys Val Ile Cys Leu
1               5                   10                  15

Phe Leu Ser Phe Gly Gln Pro Phe Phe Pro Ser Met Ile Leu Thr Val
            20                  25                  30

Gln Ala Ala Lys Ser
            35

<210> SEQ ID NO 14
<211> LENGTH: 35
<212> TYPE: PRT
<213> ORGANISM: Artificial
<220> FEATURE:
<223> OTHER INFORMATION: kuenstliche Sekretionssequenz

<400> SEQUENCE: 14

Met Lys Ile Ser Met Gln Lys Ala Asp Phe Trp Lys Lys Ala Ala Ile
1               5                   10                  15

Ser Leu Leu Val Phe Thr Met Phe Phe Thr Leu Met Met Ser Glu Thr
            20                  25                  30

Val Phe Ala
        35

<210> SEQ ID NO 15
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 15

Met Arg Lys Lys Leu Lys Trp Leu Ser Phe Leu Leu Gly Phe Ile Ile
1               5                   10                  15
```

```
Leu Leu Phe Leu Phe Lys Tyr Gln Phe Ser Asn
            20                  25
```

<210> SEQ ID NO 16
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 16

```
Met Arg Ile Phe Lys Lys Ala Val Phe Val Thr Met Ile Ser Phe Leu
1               5                   10                  15
Ile Ala Thr Val Asn Val Asn Thr Ala His Ala
            20                  25
```

<210> SEQ ID NO 17
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 17

```
Met Lys Arg Leu Leu Ser Thr Leu Leu Ile Gly Ile Met Leu Leu Thr
1               5                   10                  15
Phe Ala Pro Ser Ala Phe Ala
            20
```

<210> SEQ ID NO 18
<211> LENGTH: 21
<212> TYPE: PRT
<213> ORGANISM: Artificial
<220> FEATURE:
<223> OTHER INFORMATION: kuenstliche Sekretionssequenz

<400> SEQUENCE: 18

```
Met Lys Lys Arg Phe Phe Gly Pro Ile Ile Leu Ala Phe Ile Leu Phe
1               5                   10                  15
Ala Gly Ala Ile Ala
            20
```

<210> SEQ ID NO 19
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 19

```
Met Lys Asn Met Ser Cys Lys Leu Val Val Ser Val Thr Leu Phe Phe
1               5                   10                  15
Ser Phe Leu Thr Ile Gly Pro Leu Ala His Ala
            20                  25
```

<210> SEQ ID NO 20
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 20

```
Met Lys Lys Lys Leu Met Ile Ile Leu Leu Ile Ile Leu Ile Val Ile
1               5                   10                  15
```

Gly Ala Leu Gly Ala Ala Ala
            20

<210> SEQ ID NO 21
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 21

Met Lys Lys Ser Gln Tyr Phe Ile Val Phe Ile Cys Phe Phe Val Leu
1               5                   10                  15

Phe Ser Val His Pro Ile Ala Ala Ala Ala Ala
            20                  25

<210> SEQ ID NO 22
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 22

Met Arg Lys Asn Arg Ile Leu Ala Leu Phe Val Leu Ser Leu Gly Leu
1               5                   10                  15

Leu Ser Phe Met Val Thr Pro Val Ser Ala
            20                  25

<210> SEQ ID NO 23
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 23

Met Lys Lys Val Leu Met Ala Phe Ile Ile Cys Leu Ser Leu Ile Leu
1               5                   10                  15

Ser Val Leu Ala Ala Pro Pro Ser Gly Ala Lys Ala
            20                  25

<210> SEQ ID NO 24
<211> LENGTH: 25
<212> TYPE: PRT
<213> ORGANISM: Artificial
<220> FEATURE:
<223> OTHER INFORMATION: kuenstliche Sekretionssequenz

<400> SEQUENCE: 24

Met Lys Ser Cys Lys Gln Leu Ile Val Cys Ser Leu Ala Ala Ile Leu
1               5                   10                  15

Leu Leu Ile Pro Ser Val Ser Phe Ala
            20                  25

<210> SEQ ID NO 25
<211> LENGTH: 24
<212> TYPE: PRT
<213> ORGANISM: Artificial
<220> FEATURE:
<223> OTHER INFORMATION: kuenstliche Sekretionssequenz

<400> SEQUENCE: 25

Met Arg Ser Tyr Ile Lys Val Leu Thr Met Cys Phe Leu Gly Leu Ile

```
1               5                   10                  15
Leu Phe Val Pro Thr Ala Leu Ala
            20

<210> SEQ ID NO 26
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 26

Met Lys Lys Arg Leu Ile Ala Pro Met Leu Leu Ser Ala Ala Ser Leu
1               5                   10                  15

Ala Phe Phe Ala Met Ser Gly Ser Ala Gln Ala
            20                  25

<210> SEQ ID NO 27
<211> LENGTH: 19
<212> TYPE: PRT
<213> ORGANISM: Artificial
<220> FEATURE:
<223> OTHER INFORMATION: kuenstliche Sekretionssequenz

<400> SEQUENCE: 27

Met Lys Lys Gln Ile Ile Thr Ala Thr Thr Ala Val Val Leu Gly Ala
1               5                   10                  15

Leu Phe Ala

<210> SEQ ID NO 28
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 28

Met Lys Lys Lys Leu Ala Ala Gly Leu Thr Ala Ser Ala Ile Val Gly
1               5                   10                  15

Thr Thr Leu Val Val Thr Pro Ala Glu Ala
            20                  25

<210> SEQ ID NO 29
<211> LENGTH: 38
<212> TYPE: PRT
<213> ORGANISM: Artificial
<220> FEATURE:
<223> OTHER INFORMATION: kuenstliche Sekretionssequenz

<400> SEQUENCE: 29

Met Arg Asn Glu Arg Arg Lys Lys Lys Thr Leu Leu Leu Thr Ile Leu
1               5                   10                  15

Thr Ile Ile Gly Leu Leu Val Leu Gly Thr Gly Gly Tyr Ala Tyr Tyr
            20                  25                  30

Leu Trp His Lys Ala Ala
            35

<210> SEQ ID NO 30
<211> LENGTH: 35
<212> TYPE: PRT
<213> ORGANISM: Artificial
<220> FEATURE:
<223> OTHER INFORMATION: kuenstliche Sekretionssequenz
```

-continued

```
<400> SEQUENCE: 30

Met Asp Thr Thr Thr Ala Lys Gln Ala Ser Thr Lys Phe Val Val Leu
1               5                   10                  15

Gly Leu Leu Leu Gly Ile Leu Met Ser Ala Met Asp Asn Thr Ile Val
            20                  25                  30

Ala Thr Ala
        35

<210> SEQ ID NO 31
<211> LENGTH: 40
<212> TYPE: PRT
<213> ORGANISM: Artificial
<220> FEATURE:
<223> OTHER INFORMATION: kuenstliche Sekretionssequenz

<400> SEQUENCE: 31

Met Ala Arg Lys Lys Lys Lys His Glu Asp Glu His Val Asp Glu
1               5                   10                  15

Ser Trp Leu Val Pro Tyr Ala Asp Ile Leu Thr Leu Leu Leu Ala Leu
            20                  25                  30

Phe Ile Val Leu Tyr Ala Ser Ser
        35                  40

<210> SEQ ID NO 32
<211> LENGTH: 34
<212> TYPE: PRT
<213> ORGANISM: Artificial
<220> FEATURE:
<223> OTHER INFORMATION: kuenstliche Sekretionssequenz

<400> SEQUENCE: 32

Met Lys Leu Val Pro Arg Phe Arg Lys Gln Trp Phe Ala Tyr Leu Thr
1               5                   10                  15

Val Leu Cys Leu Ala Leu Ala Ala Ala Val Ser Phe Gly Val Pro Ala
            20                  25                  30

Lys Ala

<210> SEQ ID NO 33
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 33

Met Pro Asn Lys Arg Leu Met Leu Leu Leu Leu Cys Ile Ile Ile Leu
1               5                   10                  15

Val Ala Met Ile Gly Phe Ser
            20

<210> SEQ ID NO 34
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 34

Met Arg Asn Leu Thr Lys Thr Ser Leu Leu Leu Ala Gly Leu Cys Thr
1               5                   10                  15

Ala Ala Gln Met Val Phe Val Thr His Ala Ser Ala
            20                  25
```

<210> SEQ ID NO 35
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 35

Met Gly Leu Gly Lys Lys Leu Ser Val Ala Val Ala Ala Ser Phe Met
1               5                   10                  15

Ser Leu Ser Ile Ser Leu Pro Gly Val Gln Ala
            20                  25

<210> SEQ ID NO 36
<211> LENGTH: 29
<212> TYPE: PRT
<213> ORGANISM: Artificial
<220> FEATURE:
<223> OTHER INFORMATION: kuenstliche Sekretionssequenz

<400> SEQUENCE: 36

Met Lys Lys Trp Met Ala Gly Leu Phe Leu Ala Ala Ala Val Leu Leu
1               5                   10                  15

Cys Leu His Val Pro Gln Gln Ile Gln Gly Ala Ser Ser
            20                  25

<210> SEQ ID NO 37
<211> LENGTH: 29
<212> TYPE: PRT
<213> ORGANISM: Artificial
<220> FEATURE:
<223> OTHER INFORMATION: kuenstliche Sekretionssequenz

<400> SEQUENCE: 37

Met Lys Lys Ser Ile Lys Leu Tyr Val Ala Val Leu Leu Leu Phe Val
1               5                   10                  15

Val Ala Ser Val Pro Tyr Met His Gln Ala Ala Leu Ala
            20                  25

<210> SEQ ID NO 38
<211> LENGTH: 34
<212> TYPE: PRT
<213> ORGANISM: Artificial
<220> FEATURE:
<223> OTHER INFORMATION: kuenstliche Sekretionssequenz

<400> SEQUENCE: 38

Met Ile Gln Met Pro Lys Lys Asn Lys Phe Met Asn Arg Gly Ala Ala
1               5                   10                  15

Ile Leu Ser Ile Cys Phe Ala Leu Phe Phe Val Ile Leu Gly Arg
            20                  25                  30

Met Ala

<210> SEQ ID NO 39
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 39

Met Thr Met Leu Arg Lys Ile Ile Gly Trp Ile Leu Leu Leu Cys Ile
1               5                   10                  15

```
Ile Pro Leu Phe Ala Phe Thr Val Ile Ala
            20                  25
```

<210> SEQ ID NO 40
<211> LENGTH: 21
<212> TYPE: PRT
<213> ORGANISM: Artificial
<220> FEATURE:
<223> OTHER INFORMATION: kuenstliche Sekretionssequenz

<400> SEQUENCE: 40

```
Met Lys Lys Val Met Leu Ala Thr Ala Leu Phe Leu Gly Leu Thr Pro
1               5                   10                  15

Ala Gly Ala Asn Ala
            20
```

<210> SEQ ID NO 41
<211> LENGTH: 24
<212> TYPE: PRT
<213> ORGANISM: Artificial
<220> FEATURE:
<223> OTHER INFORMATION: kuenstliche Sekretionssequenz

<400> SEQUENCE: 41

```
Met Lys Arg Leu Cys Leu Trp Phe Thr Val Phe Ser Leu Phe Leu Val
1               5                   10                  15

Leu Leu Pro Gly Lys Ala Leu Gly
            20
```

<210> SEQ ID NO 42
<211> LENGTH: 36
<212> TYPE: PRT
<213> ORGANISM: Artificial
<220> FEATURE:
<223> OTHER INFORMATION: kuenstliche Sekretionssequenz

<400> SEQUENCE: 42

```
Met Lys Leu Lys Thr Lys Ala Ser Ile Lys Phe Gly Ile Cys Val Gly
1               5                   10                  15

Leu Leu Cys Leu Ser Ile Thr Gly Phe Thr Pro Phe Pro Asn Ser Thr
            20                  25                  30

His Ala Glu Ala
        35
```

<210> SEQ ID NO 43
<211> LENGTH: 31
<212> TYPE: PRT
<213> ORGANISM: Artificial
<220> FEATURE:
<223> OTHER INFORMATION: kuenstliche Sekretionssequenz

<400> SEQUENCE: 43

```
Met Lys Lys Met Ser Leu Phe Gln Asn Met Lys Ser Lys Leu Leu Pro
1               5                   10                  15

Ile Ala Ala Val Ser Val Leu Thr Ala Gly Ile Phe Ala Gly Ala
            20                  25                  30
```

<210> SEQ ID NO 44
<211> LENGTH: 32
<212> TYPE: PRT
<213> ORGANISM: Artificial
<220> FEATURE:
<223> OTHER INFORMATION: kuenstliche Sekretionssequenz

```
<400> SEQUENCE: 44

Met Lys Lys Phe Pro Lys Lys Leu Leu Pro Ile Ala Val Leu Ser Ser
1               5                   10                  15

Ile Ala Phe Ser Ser Leu Ala Ser Gly Ser Val Pro Glu Ala Ser Ala
            20                  25                  30

<210> SEQ ID NO 45
<211> LENGTH: 25
<212> TYPE: PRT
<213> ORGANISM: Artificial
<220> FEATURE:
<223> OTHER INFORMATION: kuenstliche Sekretionssequenz

<400> SEQUENCE: 45

Met Lys Ser Lys Trp Met Ser Gly Leu Leu Leu Val Ala Val Gly Phe
1               5                   10                  15

Ser Phe Thr Gln Val Met Val His Ala
            20                  25

<210> SEQ ID NO 46
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 46

Met Lys Leu Lys Ser Lys Leu Phe Val Ile Cys Leu Ala Ala Ala Ala
1               5                   10                  15

Ile Phe Thr Ala Ala Gly Val Ser Ala Asn Ala
            20                  25

<210> SEQ ID NO 47
<211> LENGTH: 24
<212> TYPE: PRT
<213> ORGANISM: Artificial
<220> FEATURE:
<223> OTHER INFORMATION: kuenstliche Sekretionssequenz

<400> SEQUENCE: 47

Met Lys Leu Lys Ser Lys Leu Leu Leu Ser Cys Leu Ala Leu Ser Thr
1               5                   10                  15

Val Phe Val Ala Thr Thr Ile Ala
            20

<210> SEQ ID NO 48
<211> LENGTH: 21
<212> TYPE: PRT
<213> ORGANISM: Artificial
<220> FEATURE:
<223> OTHER INFORMATION: kuenstliche Sekretionssequenz

<400> SEQUENCE: 48

Met Lys Arg Phe Leu Ile Gly Ala Gly Val Ala Ala Val Ile Leu Ser
1               5                   10                  15

Gly Trp Phe Ile Ala
            20

<210> SEQ ID NO 49
<211> LENGTH: 19
<212> TYPE: PRT
<213> ORGANISM: Artificial
<220> FEATURE:
<223> OTHER INFORMATION: kuenstliche Sekretionssequenz
```

```
<400> SEQUENCE: 49

Met Lys Lys Leu Val Leu Cys Val Ser Ile Leu Ala Val Ile Leu Ser
1               5                   10                  15

Gly Val Ala

<210> SEQ ID NO 50
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 50

Met Arg Lys Lys Ile Thr Leu Ala Cys Lys Thr Cys Gly Asn Arg Asn
1               5                   10                  15

Tyr Thr Thr Met Lys Ser Ser Ala Ser Ala
                20                  25

<210> SEQ ID NO 51
<211> LENGTH: 29
<212> TYPE: PRT
<213> ORGANISM: Artificial
<220> FEATURE:
<223> OTHER INFORMATION: kuenstliche Sekretionssequenz

<400> SEQUENCE: 51

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala
                20                  25

<210> SEQ ID NO 52
<211> LENGTH: 24
<212> TYPE: PRT
<213> ORGANISM: Artificial
<220> FEATURE:
<223> OTHER INFORMATION: kuenstliche Sekretionssequenz

<400> SEQUENCE: 52

Met Lys Lys Arg Leu Ile Gln Val Met Ile Met Phe Thr Leu Leu Leu
1               5                   10                  15

Thr Met Ala Phe Ser Ala Asp Ala
                20

<210> SEQ ID NO 53
<211> LENGTH: 31
<212> TYPE: PRT
<213> ORGANISM: Artificial
<220> FEATURE:
<223> OTHER INFORMATION: kuenstliche Sekretionssequenz

<400> SEQUENCE: 53

Met Lys Ser Lys Gly Ser Ile Met Ala Cys Leu Ile Leu Phe Ser Phe
1               5                   10                  15

Thr Ile Thr Thr Phe Ile Asn Thr Glu Thr Ile Ser Ala Phe Ser
                20                  25                  30

<210> SEQ ID NO 54
<211> LENGTH: 34
<212> TYPE: PRT
<213> ORGANISM: Artificial
<220> FEATURE:
<223> OTHER INFORMATION: kuenstliche Sekretionssequenz
```

<400> SEQUENCE: 54

Met Lys Gln Phe Ala Ile Thr Leu Ser Val Leu Cys Ala Leu Ile Leu
1               5                   10                  15

Leu Val Pro Thr Leu Leu Val Ile Pro Phe Gln His Asn Lys Glu Ala
            20                  25                  30

Gly Ala

<210> SEQ ID NO 55
<211> LENGTH: 39
<212> TYPE: PRT
<213> ORGANISM: Artificial
<220> FEATURE:
<223> OTHER INFORMATION: kuenstliche Sekretionssequenz

<400> SEQUENCE: 55

Met Arg Asn Lys Arg Asn Arg Gln Ile Val Val Ala Val Asn Gly
1               5                   10                  15

Gly Lys Ala Val Lys Ala Ile Phe Leu Phe Ile Val Ser Leu Ile Val
            20                  25                  30

Ile Phe Val Leu Ser Gly Val
        35

<210> SEQ ID NO 56
<211> LENGTH: 40
<212> TYPE: PRT
<213> ORGANISM: Artificial
<220> FEATURE:
<223> OTHER INFORMATION: kuenstliche Sekretionssequenz

<400> SEQUENCE: 56

Met Arg Glu Glu Glu Lys Lys Thr Ser Gln Val Lys Lys Leu Gln Gln
1               5                   10                  15

Phe Phe Arg Lys Arg Trp Val Phe Pro Ala Ile Tyr Leu Val Ser Ala
            20                  25                  30

Ala Ile Leu Thr Ala Val Leu
        35                  40

<210> SEQ ID NO 57
<211> LENGTH: 20
<212> TYPE: PRT
<213> ORGANISM: Artificial
<220> FEATURE:
<223> OTHER INFORMATION: kuenstliche Sekretionssequenz

<400> SEQUENCE: 57

Met Lys Lys Thr Val Ile Ile Cys Ile Tyr Ile Phe Leu Leu Leu Ser
1               5                   10                  15

Gly Ala Leu Val
            20

<210> SEQ ID NO 58
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 58

Met Gly Met Lys Lys Lys Leu Ser Leu Gly Val Ala Ser Ala Ala Leu
1               5                   10                  15

Gly Leu Ala Leu Val Gly Gly Gly Thr Trp Ala 20                  25

<210> SEQ ID NO 59
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 59

Met Asn Gln Met Lys Asp Thr Ile Leu Leu Ala Gly Leu Gly Leu Ile
1               5                   10                  15

Gly Gly Ser Ile Ala Leu Ala
            20

<210> SEQ ID NO 60
<211> LENGTH: 31
<212> TYPE: PRT
<213> ORGANISM: Artificial
<220> FEATURE:
<223> OTHER INFORMATION: kuenstliche Sekretionssequenz

<400> SEQUENCE: 60

Met Lys Lys Gly Ile Ile Arg Phe Leu Leu Val Ser Phe Val Leu Phe
1               5                   10                  15

Phe Ala Leu Ser Thr Gly Ile Thr Gly Val Gln Ala Ala Pro Ala
            20                  25                  30

<210> SEQ ID NO 61
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 61

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala
            20                  25

<210> SEQ ID NO 62
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 62

Met Arg Lys Thr Ile Phe Ala Phe Leu Thr Gly Leu Met Met Phe Gly
1               5                   10                  15

Thr Ile Thr Ala Ala Ser Ala
            20

<210> SEQ ID NO 63
<211> LENGTH: 25
<212> TYPE: PRT
<213> ORGANISM: Artificial
<220> FEATURE:
<223> OTHER INFORMATION: kuenstliche Sekretionssequenz

<400> SEQUENCE: 63

Met Lys Thr Lys Thr Leu Phe Ile Phe Ser Ala Ile Leu Thr Leu Ser
1               5                   10                  15

Ile Phe Ala Pro Asn Glu Thr Phe Ala
            20                  25

<210> SEQ ID NO 64
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 64

Met Asp Lys Phe Leu Asn Asn Arg Trp Ala Val Lys Ile Ile Ala Leu
1               5                   10                  15

Leu Phe Ala Leu Leu Leu Tyr Val Ala Val Asn Ser
            20                  25

<210> SEQ ID NO 65
<211> LENGTH: 25
<212> TYPE: PRT
<213> ORGANISM: Artificial
<220> FEATURE:
<223> OTHER INFORMATION: kuenstliche Sekretionssequenz

<400> SEQUENCE: 65

Met Lys Thr Leu Trp Lys Val Leu Lys Ile Val Phe Val Ser Leu Ala
1               5                   10                  15

Ala Leu Val Leu Leu Val Ser Val Ser
            20                  25

<210> SEQ ID NO 66
<211> LENGTH: 25
<212> TYPE: PRT
<213> ORGANISM: Artificial
<220> FEATURE:
<223> OTHER INFORMATION: kuenstliche Sekretionssequenz

<400> SEQUENCE: 66

Met Val Lys Lys Trp Leu Ile Gln Phe Ala Val Met Leu Ser Val Leu
1               5                   10                  15

Ser Thr Phe Thr Tyr Ser Ala Ser Ala
            20                  25

<210> SEQ ID NO 67
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 67

Met Lys Arg Met Ile Val Arg Met Thr Leu Pro Leu Leu Ile Val Cys
1               5                   10                  15

Leu Ala Phe Ser Ser Phe Ser Ala Ser Ala Arg Ala
            20                  25

<210> SEQ ID NO 68
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 68

Met Lys Lys Trp Ile Tyr Val Val Leu Val Leu Ser Ile Ala Gly Ile
1               5                   10                  15

Gly Gly Phe Ser Val His Ala
            20

<210> SEQ ID NO 69
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 69

Met Lys Arg Ile Thr Ile Asn Ile Ile Thr Met Phe Ile Ala Ala Ala
1               5                   10                  15

Val Ile Ser Leu Thr Gly Thr Ala Glu Ala
            20                  25

<210> SEQ ID NO 70
<211> LENGTH: 32
<212> TYPE: PRT
<213> ORGANISM: Artificial
<220> FEATURE:
<223> OTHER INFORMATION: kuenstliche Sekretionssequenz

<400> SEQUENCE: 70

Met Lys Leu Phe Asn Arg Lys Val Thr Leu Val Ser Leu Ile Leu Met
1               5                   10                  15

Ala Val Phe Gln Phe Phe Met Ala Leu Ile Lys Arg Ile Val Ile Ser
            20                  25                  30

<210> SEQ ID NO 71
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 71

Met Arg Lys Lys Arg Val Ile Thr Cys Val Met Ala Ala Ser Leu Thr
1               5                   10                  15

Leu Gly Ser Leu Leu Pro Ala Gly Tyr Ala Ser Ala
            20                  25

<210> SEQ ID NO 72
<211> LENGTH: 21
<212> TYPE: PRT
<213> ORGANISM: Artificial
<220> FEATURE:
<223> OTHER INFORMATION: kuenstliche Sekretionssequenz

<400> SEQUENCE: 72

Met Phe Lys Lys His Thr Ile Ser Leu Leu Ile Ile Phe Leu Leu Ala
1               5                   10                  15

Ser Ala Val Leu Ala
            20

<210> SEQ ID NO 73
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 73

Met Leu Lys Lys Val Ile Leu Ala Ala Phe Ile Leu Val Gly Ser Thr

```
                1               5                  10                  15
Leu Gly Ala Phe Ser Phe Ser Ser Asp Ala Ser Ala
            20                  25

<210> SEQ ID NO 74
<211> LENGTH: 21
<212> TYPE: PRT
<213> ORGANISM: Artificial
<220> FEATURE:
<223> OTHER INFORMATION: kuenstliche Sekretionssequenz

<400> SEQUENCE: 74

Met Lys Lys Arg Ile Ile Leu Leu Ala Val Ile Ile Ala Ala Ala
1               5                  10                  15

Ala Ala Gly Val Ala
            20

<210> SEQ ID NO 75
<211> LENGTH: 29
<212> TYPE: PRT
<213> ORGANISM: Artificial
<220> FEATURE:
<223> OTHER INFORMATION: kuenstliche Sekretionssequenz

<400> SEQUENCE: 75

Met Lys Lys Lys Gln Val Met Leu Ala Leu Thr Ala Ala Ala Gly Leu
1               5                  10                  15

Gly Leu Thr Ala Leu His Ser Ala Pro Ala Ala Lys Ala
            20                  25

<210> SEQ ID NO 76
<211> LENGTH: 21
<212> TYPE: PRT
<213> ORGANISM: Artificial
<220> FEATURE:
<223> OTHER INFORMATION: kuenstliche Sekretionssequenz

<400> SEQUENCE: 76

Met Lys Trp Met Cys Ser Ile Cys Cys Ala Ala Val Leu Leu Ala Gly
1               5                  10                  15

Gly Ala Ala Gln Ala
            20

<210> SEQ ID NO 77
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 77

Met Met Lys Lys Leu Phe His Ser Thr Leu Ile Val Leu Leu Phe Phe
1               5                  10                  15

Ser Phe Phe Gly Val Gln Pro Ile His Ala
            20                  25

<210> SEQ ID NO 78
<211> LENGTH: 34
<212> TYPE: PRT
<213> ORGANISM: Artificial
<220> FEATURE:
<223> OTHER INFORMATION: kuenstliche Sekretionssequenz

<400> SEQUENCE: 78
```

```
Met Arg Thr Trp Lys Arg Ile Pro Lys Thr Thr Met Leu Ile Ser Leu
1               5                   10                  15

Val Ser Pro Phe Leu Leu Ile Thr Pro Val Leu Phe Tyr Ala Ala Leu
            20                  25                  30

Ala Phe
```

<210> SEQ ID NO 79
<211> LENGTH: 21
<212> TYPE: PRT
<213> ORGANISM: Artificial
<220> FEATURE:
<223> OTHER INFORMATION: kuenstliche Sekretionssequenz

<400> SEQUENCE: 79

```
Met Lys Ser Leu Pro Tyr Thr Ile Ala Leu Leu Phe Cys Gly Leu Ile
1               5                   10                  15

Ile Val Ser Met Ala
            20
```

<210> SEQ ID NO 80
<211> LENGTH: 36
<212> TYPE: PRT
<213> ORGANISM: Artificial
<220> FEATURE:
<223> OTHER INFORMATION: kuenstliche Sekretionssequenz

<400> SEQUENCE: 80

```
Met Lys Lys Ile Val Ala Ala Ile Val Val Ile Gly Leu Val Phe Ile
1               5                   10                  15

Ala Phe Phe Tyr Leu Tyr Ser Arg Ser Gly Asp Val Tyr Gln Ser Val
            20                  25                  30

Asp Ala Asp Leu
        35
```

<210> SEQ ID NO 81
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 81

```
Met Lys Lys Ala Ala Ala Val Leu Leu Ser Leu Gly Leu Val Phe Gly
1               5                   10                  15

Phe Ser Tyr Gly Ala Gly His Val Ala Glu Ala
            20                  25
```

<210> SEQ ID NO 82
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 82

```
Met Lys Lys Glu Leu Leu Ala Ser Leu Val Leu Cys Leu Ser Leu Ser
1               5                   10                  15

Pro Leu Val Ser Thr Asn Glu Val Phe Ala
            20                  25
```

<210> SEQ ID NO 83
<211> LENGTH: 34
<212> TYPE: PRT

-continued

```
<213> ORGANISM: Artificial
<220> FEATURE:
<223> OTHER INFORMATION: kuenstliche Sekretionssequenz

<400> SEQUENCE: 83

Met Lys Lys Lys Thr Lys Ile Ile Leu Ser Leu Leu Ala Ala Leu Ile
1               5                   10                  15

Val Ile Leu Ile Val Leu Pro Val Leu Ser Pro Val Val Phe Thr Ala
            20                  25                  30

Ser Ser

<210> SEQ ID NO 84
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 84

Met Asn Phe Lys Lys Thr Val Val Ser Ala Leu Ser Ile Ser Ala Leu
1               5                   10                  15

Ala Leu Ser Val Ser Gly Val Ala Ser Ala
            20                  25

<210> SEQ ID NO 85
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 85

Met Lys Arg Leu Phe Met Lys Ala Ser Leu Val Leu Phe Ala Val Val
1               5                   10                  15

Phe Val Phe Ala Val Lys Gly Ala Pro Ala Lys Ala
            20                  25

<210> SEQ ID NO 86
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 86

Met Ala Ala Gln Thr Asp Tyr Lys Lys Gln Val Val Gly Ile Leu Leu
1               5                   10                  15

Ser Leu Ala Phe Val Leu Phe Val Phe Ser
            20                  25

<210> SEQ ID NO 87
<211> LENGTH: 33
<212> TYPE: PRT
<213> ORGANISM: Artificial
<220> FEATURE:
<223> OTHER INFORMATION: kuenstliche Sekretionssequenz

<400> SEQUENCE: 87

Met Lys Lys Val Trp Ile Gly Ile Gly Ile Ala Val Ile Val Ala Leu
1               5                   10                  15

Phe Val Gly Ile Asn Ile Tyr Arg Ser Ala Ala Pro Thr Ser Gly Ser
            20                  25                  30

Ala
```

```
<210> SEQ ID NO 88
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 88

Met Leu Lys Lys Lys Trp Met Val Gly Leu Leu Ala Gly Cys Leu Ala
1               5                   10                  15

Ala Gly Gly Phe Ser Tyr Asn Ala Phe Ala
            20                  25

<210> SEQ ID NO 89
<211> LENGTH: 21
<212> TYPE: PRT
<213> ORGANISM: Artificial
<220> FEATURE:
<223> OTHER INFORMATION: kuenstliche Sekretionssequenz

<400> SEQUENCE: 89

Met Thr Thr Lys Phe Thr Ala Leu Ala Val Phe Leu Leu Cys Phe Met
1               5                   10                  15

Pro Ala Ala Lys Ile
            20

<210> SEQ ID NO 90
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 90

Met Leu Thr Lys Arg Leu Leu Thr Ile Tyr Ile Met Leu Leu Gly Leu
1               5                   10                  15

Ile Ala Trp Phe Pro Gly Ala Ala Gln Ala
            20                  25

<210> SEQ ID NO 91
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 91

Met Lys Lys Ala Phe Ile Leu Ser Ala Ala Ala Val Gly Leu Phe
1               5                   10                  15

Thr Phe Gly Gly Val Gln Gln Ala Ser Ala
            20                  25

<210> SEQ ID NO 92
<211> LENGTH: 31
<212> TYPE: PRT
<213> ORGANISM: Artificial
<220> FEATURE:
<223> OTHER INFORMATION: kuenstliche Sekretionssequenz

<400> SEQUENCE: 92

Met Lys Lys Thr Phe Val Lys Lys Ala Met Leu Thr Thr Ala Ala Met
1               5                   10                  15

Thr Ser Ala Ala Leu Leu Thr Phe Gly Pro Asp Ala Ala Ser Ala
```

20                  25                  30

<210> SEQ ID NO 93
<211> LENGTH: 35
<212> TYPE: PRT
<213> ORGANISM: Artificial
<220> FEATURE:
<223> OTHER INFORMATION: kuenstliche Sekretionssequenz

<400> SEQUENCE: 93

Met Leu Arg Lys Lys His Phe Ser Trp Met Leu Val Ile Leu Ile Leu
1               5                   10                  15

Ile Ala Val Leu Ser Phe Ile Lys Leu Pro Tyr Tyr Ile Thr Lys Pro
                20                  25                  30

Gly Glu Ala
        35

<210> SEQ ID NO 94
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 94

Met Lys Lys Ile Gly Leu Leu Phe Met Leu Cys Leu Ala Ala Leu Phe
1               5                   10                  15

Thr Ile Gly Phe Pro Ala Gln Gln Ala Asp Ala
                20                  25

<210> SEQ ID NO 95
<211> LENGTH: 37
<212> TYPE: PRT
<213> ORGANISM: Artificial
<220> FEATURE:
<223> OTHER INFORMATION: kuenstliche Sekretionssequenz

<400> SEQUENCE: 95

Met Ser Gly Lys Lys Glu Ser Gly Lys Phe Arg Ser Val Leu Leu
1               5                   10                  15

Ile Ile Ile Leu Pro Leu Met Phe Leu Ile Ala Gly Gly Ile Val
                20                  25                  30

Leu Trp Ala Ala Gly
        35

<210> SEQ ID NO 96
<211> LENGTH: 35
<212> TYPE: PRT
<213> ORGANISM: Artificial
<220> FEATURE:
<223> OTHER INFORMATION: kuenstliche Sekretionssequenz

<400> SEQUENCE: 96

Met Arg Gly Lys Ser Ala Val Leu Leu Ser Leu Ile Met Leu Ile Ala
1               5                   10                  15

Gly Phe Leu Ile Ser Phe Ser Phe Gln Met Thr Lys Glu Asn Asn Lys
                20                  25                  30

Ser Ala Ala
        35

<210> SEQ ID NO 97
<211> LENGTH: 33
<212> TYPE: PRT

```
<213> ORGANISM: Artificial
<220> FEATURE:
<223> OTHER INFORMATION: kuenstliche Sekretionssequenz

<400> SEQUENCE: 97

Met Tyr Lys Lys Phe Val Pro Phe Ala Val Phe Leu Phe Leu Phe Phe
1               5                   10                  15

Val Ser Phe Glu Met Met Glu Asn Pro His Ala Leu Asp Tyr Ile Gly
            20                  25                  30

Ala

<210> SEQ ID NO 98
<211> LENGTH: 42
<212> TYPE: PRT
<213> ORGANISM: Artificial
<220> FEATURE:
<223> OTHER INFORMATION: kuenstliche Sekretionssequenz

<400> SEQUENCE: 98

Met Ala Lys Pro Leu Ser Lys Gly Gly Ile Leu Val Lys Val Leu
1               5                   10                  15

Ile Ala Gly Ala Val Gly Thr Ala Val Leu Phe Gly Thr Leu Ser Ser
            20                  25                  30

Gly Ile Pro Gly Leu Pro Ala Ala Asp Ala
        35                  40

<210> SEQ ID NO 99
<211> LENGTH: 25
<212> TYPE: PRT
<213> ORGANISM: Artificial
<220> FEATURE:
<223> OTHER INFORMATION: kuenstliche Sekretionssequenz

<400> SEQUENCE: 99

Met Arg Phe Thr Lys Val Val Gly Phe Leu Ser Val Leu Gly Leu Ala
1               5                   10                  15

Ala Val Phe Pro Leu Thr Ala Gln Ala
            20                  25

<210> SEQ ID NO 100
<211> LENGTH: 32
<212> TYPE: PRT
<213> ORGANISM: Artificial
<220> FEATURE:
<223> OTHER INFORMATION: kuenstliche Sekretionssequenz

<400> SEQUENCE: 100

Met Ile Pro Arg Ile Lys Lys Thr Ile Cys Val Leu Leu Val Cys Phe
1               5                   10                  15

Thr Met Leu Ser Val Met Leu Gly Pro Gly Ala Thr Glu Val Leu Ala
            20                  25                  30

<210> SEQ ID NO 101
<211> LENGTH: 30
<212> TYPE: PRT
<213> ORGANISM: Artificial
<220> FEATURE:
<223> OTHER INFORMATION: kuenstliche Sekretionssequenz

<400> SEQUENCE: 101

Met Lys Val Cys Gln Lys Ser Ile Val Arg Phe Leu Val Ser Leu Ile
1               5                   10                  15

Ile Gly Thr Phe Val Ile Ser Val Pro Phe Met Ala Asn Ala
```

```
                    20                  25                  30

<210> SEQ ID NO 102
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 102

Met Glu Leu Ser Phe Thr Lys Ile Leu Val Ile Leu Phe Val Gly Phe
1               5                   10                  15

Leu Val Phe Gly Pro Asp Lys Leu Pro Ala Leu Gly
            20                  25

<210> SEQ ID NO 103
<211> LENGTH: 24
<212> TYPE: PRT
<213> ORGANISM: Artificial
<220> FEATURE:
<223> OTHER INFORMATION: kuenstliche Sekretionssequenz

<400> SEQUENCE: 103

Met Lys Lys Met Leu Met Leu Ala Phe Thr Phe Leu Leu Ala Leu Thr
1               5                   10                  15

Ile His Val Gly Glu Ala Ser Ala
            20

<210> SEQ ID NO 104
<211> LENGTH: 25
<212> TYPE: PRT
<213> ORGANISM: Artificial
<220> FEATURE:
<223> OTHER INFORMATION: kuenstliche Sekretionssequenz

<400> SEQUENCE: 104

Met Lys Ile Arg Lys Ile Leu Leu Ser Ser Ala Leu Ser Phe Gly Met
1               5                   10                  15

Leu Ile Ser Ala Val Pro Ala Leu Ala
            20                  25

<210> SEQ ID NO 105
<211> LENGTH: 21
<212> TYPE: PRT
<213> ORGANISM: Artificial
<220> FEATURE:
<223> OTHER INFORMATION: kuenstliche Sekretionssequenz

<400> SEQUENCE: 105

Met Lys Leu Glu Arg Leu Leu Ala Met Val Val Leu Leu Ile Ser Lys
1               5                   10                  15

Lys Gln Val Gln Ala
            20

<210> SEQ ID NO 106
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 106

Met Lys Lys Lys Arg Lys Gly Cys Phe Ala Ala Ala Gly Phe Met Met
1               5                   10                  15
```

Ile Phe Val Phe Val Ile Ala
            20

<210> SEQ ID NO 107
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 107

Met Lys Lys Thr Ile Met Ser Phe Val Ala Val Ala Ala Leu Ser Thr
1               5                   10                  15

Thr Ala Phe Gly Ala His Ala
            20

<210> SEQ ID NO 108
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 108

Met Lys Val Pro Lys Thr Met Leu Leu Ser Thr Ala Ala Gly Leu Leu
1               5                   10                  15

Leu Ser Leu Thr Ala Thr Ser Val Ser Ala
            20                  25

<210> SEQ ID NO 109
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 109

Met Lys Lys Lys Ile Val Ala Gly Leu Ala Val Ser Ala Val Val Gly
1               5                   10                  15

Ser Ser Met Ala Ala Ala Pro Ala Glu Ala
            20                  25

<210> SEQ ID NO 110
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 110

Met Lys Lys Arg Ile Thr Tyr Ser Leu Leu Ala Leu Leu Ala Val Val
1               5                   10                  15

Ala Phe Ala Phe Thr Asp Ser Ser Lys Ala Lys Ala
            20                  25

<210> SEQ ID NO 111
<211> LENGTH: 25
<212> TYPE: PRT
<213> ORGANISM: Artificial
<220> FEATURE:
<223> OTHER INFORMATION: kuenstliche Sekretionssequenz

<400> SEQUENCE: 111

Met Lys Lys Arg Leu Ile Gly Phe Leu Val Leu Val Pro Ala Leu Ile
1               5                   10                  15

```
Met Ser Gly Ile Thr Leu Ile Glu Ala
            20                  25

<210> SEQ ID NO 112
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 112

Met Lys Lys Trp Ile Val Leu Phe Leu Val Leu Ile Ala Ala Ala Ile
1               5                   10                  15

Ser Ile Phe Val Tyr Val Ser Thr Gly Ser Glu
            20                  25

<210> SEQ ID NO 113
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 113

Met Arg Lys Lys Arg Val Ile Thr Cys Val Met Ala Ala Ser Leu Thr
1               5                   10                  15

Leu Gly Ser Leu Leu Pro Ala Gly Tyr Ala Thr Ala
            20                  25

<210> SEQ ID NO 114
<211> LENGTH: 21
<212> TYPE: PRT
<213> ORGANISM: Artificial
<220> FEATURE:
<223> OTHER INFORMATION: kuenstliche Sekretionssequenz

<400> SEQUENCE: 114

Met Lys Lys Leu Ile Met Ala Leu Val Ile Leu Gly Ala Leu Gly Thr
1               5                   10                  15

Ser Tyr Ile Ser Ala
            20

<210> SEQ ID NO 115
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 115

Met Lys Arg Phe Ile Leu Val Leu Ser Phe Leu Ser Ile Ile Val Ala
1               5                   10                  15

Tyr Pro Ile Gln Thr Asn Ala
            20

<210> SEQ ID NO 116
<211> LENGTH: 25
<212> TYPE: PRT
<213> ORGANISM: Artificial
<220> FEATURE:
<223> OTHER INFORMATION: kuenstliche Sekretionssequenz

<400> SEQUENCE: 116

Met Lys Leu Arg Lys Val Leu Thr Gly Ser Val Leu Ser Leu Gly Leu
```

```
1               5                   10                  15
Leu Val Ser Ala Ser Pro Ala Phe Ala
            20                  25
```

<210> SEQ ID NO 117
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 117

```
Met Lys Leu Ser Val Lys Ile Ala Gly Val Leu Thr Val Ala Ala
1               5                   10                  15

Ala Met Thr Ala Lys Met Tyr Ala Thr Ala
            20                  25
```

<210> SEQ ID NO 118
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 118

```
Met Asn Asn Asn Lys Leu Leu Leu Val Asp Gly Met Ala Leu Leu Phe
1               5                   10                  15

Arg Ala Phe Phe Ala Thr Ala
            20
```

<210> SEQ ID NO 119
<211> LENGTH: 29
<212> TYPE: PRT
<213> ORGANISM: Artificial
<220> FEATURE:
<223> OTHER INFORMATION: kuenstliche Sekretionssequenz

<400> SEQUENCE: 119

```
Met Lys Leu Trp Met Arg Lys Thr Leu Val Val Leu Phe Thr Ile Val
1               5                   10                  15

Thr Phe Gly Leu Val Ser Pro Pro Ala Ala Leu Met Ala
            20                  25
```

<210> SEQ ID NO 120
<211> LENGTH: 32
<212> TYPE: PRT
<213> ORGANISM: Artificial
<220> FEATURE:
<223> OTHER INFORMATION: kuenstliche Sekretionssequenz

<400> SEQUENCE: 120

```
Met Arg Lys Lys Ala Leu Ile Phe Thr Val Ile Phe Gly Ile Ile Phe
1               5                   10                  15

Leu Ala Val Leu Leu Val Ser Ala Ser Ile Tyr Lys Ser Ala Met Ala
            20                  25                  30
```

<210> SEQ ID NO 121
<211> LENGTH: 35
<212> TYPE: PRT
<213> ORGANISM: Artificial
<220> FEATURE:
<223> OTHER INFORMATION: kuenstliche Sekretionssequenz

<400> SEQUENCE: 121

Met Asn Lys Trp Lys Arg Leu Phe Phe Ile Leu Leu Ala Ile Asn Phe
1               5                   10                  15

Ile Leu Ala Ala Gly Phe Val Ala Leu Val Leu Leu Pro Gly Glu Gln
            20                  25                  30

Ala Gln Val
35

<210> SEQ ID NO 122
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 122

Met Lys Lys Ile Trp Ile Gly Met Leu Ala Ala Ala Val Leu Leu
1               5                   10                  15

Met Val Pro Lys Val Ser Leu Ala Asp Ala
            20                  25

<210> SEQ ID NO 123
<211> LENGTH: 38
<212> TYPE: PRT
<213> ORGANISM: Artificial
<220> FEATURE:
<223> OTHER INFORMATION: kuenstliche Sekretionssequenz

<400> SEQUENCE: 123

Met Gly Arg Ile Lys Thr Lys Ile Thr Ile Leu Leu Val Leu Leu
1               5                   10                  15

Leu Leu Ala Gly Gly Tyr Met Tyr Ile Asn Asp Ile Glu Leu Lys Asp
            20                  25                  30

Val Pro Thr Ala Ile Gly
        35

<210> SEQ ID NO 124
<211> LENGTH: 38
<212> TYPE: PRT
<213> ORGANISM: Artificial
<220> FEATURE:
<223> OTHER INFORMATION: kuenstliche Sekretionssequenz

<400> SEQUENCE: 124

Met Lys Arg Leu Thr Leu Val Cys Ser Thr Val Phe Ile Leu Phe Ile
1               5                   10                  15

Leu Phe Tyr Asp Leu Lys Ile Gly Thr Ile Pro Ile Gln Asp Leu Pro
            20                  25                  30

Val Tyr Glu Ala Ser Ala
        35

<210> SEQ ID NO 125
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 125

Met Lys Gln Gly Lys Phe Ser Val Phe Leu Ile Leu Leu Leu Met Leu
1               5                   10                  15

Thr Leu Val Val Ala Pro Lys Gly Lys Ala Glu Ala
            20                  25

<210> SEQ ID NO 126
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 126

Met Phe Lys Lys Leu Leu Leu Ala Thr Ser Ala Leu Thr Phe Ser Leu
1               5                   10                  15

Ser Leu Val Leu Pro Leu Asp Gly His Ala Lys Ala
            20                  25

<210> SEQ ID NO 127
<211> LENGTH: 43
<212> TYPE: PRT
<213> ORGANISM: Artificial
<220> FEATURE:
<223> OTHER INFORMATION: kuenstliche Sekretionssequenz

<400> SEQUENCE: 127

Met Phe Arg Leu Phe His Asn Gln Gln Lys Ala Lys Thr Lys Leu Lys
1               5                   10                  15

Val Leu Leu Ile Phe Gln Leu Ser Val Ile Phe Ser Leu Thr Ala Ala
            20                  25                  30

Ile Cys Leu Gln Phe Ser Asp Asp Thr Ser Ala
        35                  40

<210> SEQ ID NO 128
<211> LENGTH: 34
<212> TYPE: PRT
<213> ORGANISM: Artificial
<220> FEATURE:
<223> OTHER INFORMATION: kuenstliche Sekretionssequenz

<400> SEQUENCE: 128

Met Thr Lys Arg Gly Ile Gln Ala Phe Ala Gly Gly Ile Ile Leu Ala
1               5                   10                  15

Thr Ala Val Leu Ala Ala Val Phe Tyr Leu Thr Asp Glu Asp Gln Ala
            20                  25                  30

Ala Ala

<210> SEQ ID NO 129
<211> LENGTH: 22
<212> TYPE: PRT
<213> ORGANISM: Artificial
<220> FEATURE:
<223> OTHER INFORMATION: kuenstliche Sekretionssequenz

<400> SEQUENCE: 129

Met Met Ile Lys Gln Cys Val Ile Cys Leu Ser Leu Leu Val Phe Gly
1               5                   10                  15

Thr Thr Ala Ala His Ala
            20

<210> SEQ ID NO 130
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 130

-continued

Met Thr Leu Thr Lys Leu Lys Met Leu Ser Met Leu Thr Val Met Ile
1               5                   10                  15

Ala Ser Leu Phe Ile Phe Ser Ser Gln Ala Leu Ala
            20                  25

<210> SEQ ID NO 131
<211> LENGTH: 33
<212> TYPE: PRT
<213> ORGANISM: Artificial
<220> FEATURE:
<223> OTHER INFORMATION: kuenstliche Sekretionssequenz

<400> SEQUENCE: 131

Met Tyr Ile Asn Gln Gln Lys Lys Ser Phe Phe Asn Lys Lys Arg Ile
1               5                   10                  15

Ile Leu Ser Ser Ile Val Val Leu Phe Leu Thr Ile Gly Gly Ala Phe
            20                  25                  30

Leu

<210> SEQ ID NO 132
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 132

Met Lys Ile Ser Lys Arg Met Lys Leu Ala Val Ile Ala Phe Leu Ile
1               5                   10                  15

Val Phe Phe Leu Leu Leu Arg Leu Ala Glu Ile
            20                  25

<210> SEQ ID NO 133
<211> LENGTH: 37
<212> TYPE: PRT
<213> ORGANISM: Artificial
<220> FEATURE:
<223> OTHER INFORMATION: kuenstliche Sekretionssequenz

<400> SEQUENCE: 133

Met Ser Asn Asn Gln Ser Arg Tyr Glu Asn Arg Asp Lys Arg Arg Lys
1               5                   10                  15

Ala Asn Leu Val Leu Asn Ile Leu Ile Ala Ile Val Ser Ile Leu Ile
            20                  25                  30

Val Val Val Ala Ala
        35

<210> SEQ ID NO 134
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 134

Met Asn Lys Lys Tyr Phe Val Leu Ile Val Cys Ile Ile Phe Thr Ser
1               5                   10                  15

Ala Leu Phe Pro Thr Phe Ser Ser Val Thr Ala
            20                  25

<210> SEQ ID NO 135
<211> LENGTH: 30
<212> TYPE: PRT

<213> ORGANISM: Artificial
<220> FEATURE:
<223> OTHER INFORMATION: kuenstliche Sekretionssequenz

<400> SEQUENCE: 135

Met Lys Arg Lys Leu Leu Ser Ser Leu Ala Ile Ser Ala Leu Ser Leu
1               5                   10                  15

Gly Leu Leu Val Ser Ala Pro Thr Ala Ser Phe Ala Ala Glu
            20                  25                  30

<210> SEQ ID NO 136
<211> LENGTH: 37
<212> TYPE: PRT
<213> ORGANISM: Artificial
<220> FEATURE:
<223> OTHER INFORMATION: kuenstliche Sekretionssequenz

<400> SEQUENCE: 136

Met Ile Thr Asp Ile Phe Lys Pro Gly Cys Arg Lys Leu Cys Val Phe
1               5                   10                  15

Asn Met Lys Gly Asp Tyr Phe Val Lys Val Leu Leu Ser Ala Leu Leu
            20                  25                  30

Leu Leu Leu Phe Ala
        35

<210> SEQ ID NO 137
<211> LENGTH: 35
<212> TYPE: PRT
<213> ORGANISM: Artificial
<220> FEATURE:
<223> OTHER INFORMATION: kuenstliche Sekretionssequenz

<400> SEQUENCE: 137

Met Pro Arg Tyr Arg Gly Pro Phe Arg Lys Arg Gly Pro Leu Pro Phe
1               5                   10                  15

Arg Tyr Val Met Leu Leu Ser Val Val Phe Phe Ile Leu Ser Thr Thr
            20                  25                  30

Val Ser Leu
        35

<210> SEQ ID NO 138
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 138

Met Thr Lys Lys Ala Trp Phe Leu Pro Leu Val Cys Val Leu Leu Ile
1               5                   10                  15

Ser Gly Trp Leu Ala Pro Ala Ala Ser Ala Ser Ala
            20                  25

<210> SEQ ID NO 139
<211> LENGTH: 31
<212> TYPE: PRT
<213> ORGANISM: Artificial
<220> FEATURE:
<223> OTHER INFORMATION: kuenstliche Sekretionssequenz

<400> SEQUENCE: 139

Met His Leu Ile Arg Ala Ala Gly Ala Val Cys Leu Ala Val Val Leu
1               5                   10                  15

```
Ile Ala Gly Cys Arg Phe Asn Glu Asp Gln His Gln Ala Glu Gly
            20                  25                  30
```

<210> SEQ ID NO 140
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 140

```
Met Lys Lys Trp Leu Ile Ile Ala Val Ser Leu Ala Ile Ala Ile Val
1               5                   10                  15

Leu Phe Met Tyr Thr Lys Gly Glu Ala Lys Ala
            20                  25
```

<210> SEQ ID NO 141
<211> LENGTH: 30
<212> TYPE: PRT
<213> ORGANISM: Artificial
<220> FEATURE:
<223> OTHER INFORMATION: kuenstliche Sekretionssequenz

<400> SEQUENCE: 141

```
Met Arg Lys Ser Leu Ile Thr Leu Gly Leu Ala Ser Val Ile Gly Thr
1               5                   10                  15

Ser Ser Phe Leu Ile Pro Phe Thr Ser Lys Thr Ala Ser Ala
            20                  25                  30
```

<210> SEQ ID NO 142
<211> LENGTH: 25
<212> TYPE: PRT
<213> ORGANISM: Artificial
<220> FEATURE:
<223> OTHER INFORMATION: kuenstliche Sekretionssequenz

<400> SEQUENCE: 142

```
Met Asn Tyr Ile Lys Ala Gly Lys Trp Leu Thr Val Phe Leu Thr Phe
1               5                   10                  15

Leu Gly Ile Leu Leu Phe Ile Asp Leu
            20                  25
```

<210> SEQ ID NO 143
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 143

```
Met Lys Arg Ile Arg Ile Pro Met Thr Leu Ala Leu Ser Ala Ala Leu
1               5                   10                  15

Thr Ile Ala Pro Leu Ser Phe Ala Ser Ala
            20                  25
```

<210> SEQ ID NO 144
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 144

```
Met Lys Lys Lys Gln Gln Ser Ser Ala Lys Phe Ala Val Ile Leu Thr
1               5                   10                  15
```

```
Val Val Trp Val Leu Ala Ala Ile Val
        20              25

<210> SEQ ID NO 145
<211> LENGTH: 20
<212> TYPE: PRT
<213> ORGANISM: Artificial
<220> FEATURE:
<223> OTHER INFORMATION: kuenstliche Sekretionssequenz

<400> SEQUENCE: 145

Met Arg Lys Tyr Thr Val Ile Ala Ser Ile Leu Ser Phe Leu Ser Val
1               5                   10                  15

Leu Ser Gly Gly
        20

<210> SEQ ID NO 146
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 146

Met Lys Lys Ile Val Ser Ile Leu Phe Met Phe Gly Leu Val Met Gly
1               5                   10                  15

Phe Ser Gln Phe Gln Pro Ser Thr Val Phe Ala
        20                  25

<210> SEQ ID NO 147
<211> LENGTH: 24
<212> TYPE: PRT
<213> ORGANISM: Artificial
<220> FEATURE:
<223> OTHER INFORMATION: kuenstliche Sekretionssequenz

<400> SEQUENCE: 147

Met Lys Thr Leu Arg Thr Leu Cys Val Met Ile Leu Ser Gly Val Ile
1               5                   10                  15

Phe Phe Gly Leu Lys Ile Asp Ala
        20

<210> SEQ ID NO 148
<211> LENGTH: 31
<212> TYPE: PRT
<213> ORGANISM: Artificial
<220> FEATURE:
<223> OTHER INFORMATION: kuenstliche Sekretionssequenz

<400> SEQUENCE: 148

Met Lys Lys Leu Leu Thr Val Met Thr Met Ala Val Leu Thr Ala Gly
1               5                   10                  15

Thr Leu Leu Leu Pro Ala Gln Ser Val Thr Pro Ala Ala His Ala
        20                  25                  30

<210> SEQ ID NO 149
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 149

Met Lys Arg Leu Leu Val Ser Leu Arg Val Trp Met Val Phe Leu Met
```

```
                1               5                   10                  15
Asn Trp Val Thr Pro Asp Arg Lys Thr Ala Arg Ala
                20                  25

<210> SEQ ID NO 150
<211> LENGTH: 22
<212> TYPE: PRT
<213> ORGANISM: Artificial
<220> FEATURE:
<223> OTHER INFORMATION: kuenstliche Sekretionssequenz

<400> SEQUENCE: 150

Met Lys Val Phe Ile Ile Leu Gly Ala Ile Asn Ala Leu Leu Ala Val
1               5                   10                  15

Gly Leu Gly Ala Phe Gly
            20

<210> SEQ ID NO 151
<211> LENGTH: 25
<212> TYPE: PRT
<213> ORGANISM: Artificial
<220> FEATURE:
<223> OTHER INFORMATION: kuenstliche Sekretionssequenz

<400> SEQUENCE: 151

Met Lys Gly Asn Ile Tyr Ser Leu Phe Val Leu Ile Ala Ala Phe Phe
1               5                   10                  15

Trp Gly Thr Thr Gly Thr Val Gln Ala
            20                  25

<210> SEQ ID NO 152
<211> LENGTH: 24
<212> TYPE: PRT
<213> ORGANISM: Artificial
<220> FEATURE:
<223> OTHER INFORMATION: kuenstliche Sekretionssequenz

<400> SEQUENCE: 152

Met Lys Met Lys Ser Gly Met Glu Gln Ala Val Ser Val Leu Leu Leu
1               5                   10                  15

Leu Ser Arg Leu Pro Val Gln Ala
            20

<210> SEQ ID NO 153
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 153

Met Lys Val Phe Ile Val Ile Met Ile Ile Val Val Ile Phe Phe Ala
1               5                   10                  15

Leu Ile Leu Leu Asp Ile Phe Met Gly Arg Ala
            20                  25

<210> SEQ ID NO 154
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 154
```

```
Met Lys Lys Gln Val Ser His Ala Ile Ile Ser Val Met Leu
1               5                   10                  15

Ser Phe Val Ile Ala Val Phe His Thr Ile His Ala
            20                  25
```

<210> SEQ ID NO 155
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 155

```
Met Lys Lys Arg Phe Ser Leu Ile Met Met Thr Gly Leu Leu Phe Gly
1               5                   10                  15

Leu Thr Ser Pro Ala Phe Ala
            20
```

<210> SEQ ID NO 156
<211> LENGTH: 23
<212> TYPE: PRT
<213> ORGANISM: Artificial
<220> FEATURE:
<223> OTHER INFORMATION: kuenstliche Sekretionssequenz

<400> SEQUENCE: 156

```
Met Lys Lys Leu Leu Ala Ala Gly Ile Ile Gly Leu Leu Thr Val Ser
1               5                   10                  15

Ile Ala Ser Pro Ser Phe Ala
            20
```

<210> SEQ ID NO 157
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 157

```
Met Arg Lys Trp Tyr Phe Ile Leu Leu Ala Gly Val Leu Thr Ser Val
1               5                   10                  15

Ile Leu Ala Phe Val Tyr Asp Lys Thr Lys Ala
            20                  25
```

<210> SEQ ID NO 158
<211> LENGTH: 30
<212> TYPE: PRT
<213> ORGANISM: Artificial
<220> FEATURE:
<223> OTHER INFORMATION: kuenstliche Sekretionssequenz

<400> SEQUENCE: 158

```
Met Gly Glu Ser Thr Ser Leu Lys Glu Ile Leu Ser Thr Leu Thr Lys
1               5                   10                  15

Arg Ile Leu Leu Ile Met Ile Val Thr Ala Ala Ala Thr Ala
            20                  25                  30
```

<210> SEQ ID NO 159
<211> LENGTH: 28
<212> TYPE: PRT
<213> ORGANISM: Artificial
<220> FEATURE:
<223> OTHER INFORMATION: kuenstliche Sekretionssequenz

<400> SEQUENCE: 159

```
Met Lys Phe Leu Leu Ser Val Ile Ala Gly Leu Leu Ile Leu Ala Leu
1               5                   10                  15

Tyr Leu Phe Trp Lys Val Gln Pro Pro Val Trp Ile
            20                  25
```

<210> SEQ ID NO 160
<211> LENGTH: 30
<212> TYPE: PRT
<213> ORGANISM: Artificial
<220> FEATURE:
<223> OTHER INFORMATION: kuenstliche Sekretionssequenz

<400> SEQUENCE: 160

```
Met Asn Lys Pro Thr Lys Leu Phe Ser Thr Leu Ala Leu Ala Ala Gly
1               5                   10                  15

Met Thr Ala Ala Ala Ala Gly Gly Ala Gly Thr Ile His Ala
            20                  25                  30
```

<210> SEQ ID NO 161
<211> LENGTH: 22
<212> TYPE: PRT
<213> ORGANISM: Artificial
<220> FEATURE:
<223> OTHER INFORMATION: kuenstliche Sekretionssequenz

<400> SEQUENCE: 161

```
Met Lys Phe Val Lys Ala Ile Trp Pro Phe Val Ala Val Ala Ile Val
1               5                   10                  15

Phe Met Phe Met Ser Ala
            20
```

<210> SEQ ID NO 162
<211> LENGTH: 34
<212> TYPE: PRT
<213> ORGANISM: Artificial
<220> FEATURE:
<223> OTHER INFORMATION: kuenstliche Sekretionssequenz

<400> SEQUENCE: 162

```
Met Asn Thr Leu Ala Asn Trp Lys Lys Phe Leu Leu Val Ala Val Ile
1               5                   10                  15

Ile Cys Phe Leu Val Pro Ile Met Thr Lys Ala Glu Ile Ala Glu Ala
            20                  25                  30

Asp Thr
```

<210> SEQ ID NO 163
<211> LENGTH: 39
<212> TYPE: PRT
<213> ORGANISM: Artificial
<220> FEATURE:
<223> OTHER INFORMATION: kuenstliche Sekretionssequenz

<400> SEQUENCE: 163

```
Met Glu Glu Arg Ser Gln Arg Arg Lys Lys Arg Lys Leu Lys Lys
1               5                   10                  15

Trp Val Lys Val Val Ala Gly Leu Met Ala Phe Leu Val Ile Ala Ala
            20                  25                  30

Gly Ser Val Gly Ala Tyr Ala
            35
```

<210> SEQ ID NO 164
<211> LENGTH: 41

-continued

<212> TYPE: PRT
<213> ORGANISM: Artificial
<220> FEATURE:
<223> OTHER INFORMATION: kuenstliche Sekretionssequenz

<400> SEQUENCE: 164

Met Val Lys Ser Phe Arg Met Lys Ala Leu Ile Ala Gly Ala Ala Val
1               5                   10                  15

Ala Ala Ala Val Ser Ala Gly Ala Val Ser Asp Val Pro Ala Ala Lys
            20                  25                  30

Val Leu Gln Pro Thr Ala Ala Tyr Ala
        35                  40

<210> SEQ ID NO 165
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 165

Met Phe Asn Arg Leu Phe Arg Val Cys Phe Leu Ala Ala Leu Ile Met
1               5                   10                  15

Ala Phe Thr Leu Pro Asn Ser Val Tyr Ala
            20                  25

<210> SEQ ID NO 166
<211> LENGTH: 32
<212> TYPE: PRT
<213> ORGANISM: Artificial
<220> FEATURE:
<223> OTHER INFORMATION: kuenstliche Sekretionssequenz

<400> SEQUENCE: 166

Met Lys Trp Asn Asn Met Leu Lys Ala Ala Gly Ile Ala Val Leu Leu
1               5                   10                  15

Phe Ser Val Phe Ala Tyr Ala Ala Pro Ser Leu Lys Ala Val Gln Ala
            20                  25                  30

<210> SEQ ID NO 167
<211> LENGTH: 26
<212> TYPE: PRT
<213> ORGANISM: Artificial
<220> FEATURE:
<223> OTHER INFORMATION: kuenstliche Sekretionssequenz

<400> SEQUENCE: 167

Met Val Tyr Gln Thr Lys Arg Asp Val Pro Val Thr Leu Met Ile Val
1               5                   10                  15

Phe Leu Thr Leu Leu Ile Gln Ala Asp Ala
            20                  25

<210> SEQ ID NO 168
<211> LENGTH: 30
<212> TYPE: PRT
<213> ORGANISM: Artificial
<220> FEATURE:
<223> OTHER INFORMATION: kuenstliche Sekretionssequenz

<400> SEQUENCE: 168

Met Asn Lys Phe Leu Lys Ser Asn Phe Arg Phe Leu Leu Ala Ala Ala
1               5                   10                  15

Leu Gly Ile Ser Leu Leu Ala Ser Ser Asn Phe Ile Lys Ala
            20                  25                  30

<210> SEQ ID NO 169
<211> LENGTH: 27
<212> TYPE: PRT
<213> ORGANISM: Artificial
<220> FEATURE:
<223> OTHER INFORMATION: kuenstliche Sekretionssequenz

<400> SEQUENCE: 169

Met Lys Lys Trp Met Ile Thr Ile Ala Met Leu Ile Leu Ala Gly Ile
1               5                   10                  15

Ala Leu Phe Val Phe Ile Ser Pro Leu Lys Ser
            20                  25

<210> SEQ ID NO 170
<211> LENGTH: 33
<212> TYPE: PRT
<213> ORGANISM: Bacillus amyloliquefaciens

<400> SEQUENCE: 170

Met Phe Glu Lys Arg Phe Lys Thr Ser Leu Leu Pro Leu Phe Ala Gly
1               5                   10                  15

Phe Leu Leu Leu Phe His Leu Val Leu Ser Gly Pro Ala Ala Ala Asn
            20                  25                  30

Ala

<210> SEQ ID NO 171
<211> LENGTH: 947
<212> TYPE: DNA
<213> ORGANISM: Bacillus subtilis

<400> SEQUENCE: 171
tgtcatcgta ccgtatttgt cgtaggcatt gtagagcttt cgcaaaatat catcttgttc      60
cacaaattta tcgcctgttt ttctgatgaa aatctcattg tcactcagct tagtgacgag     120 cgccttttcct gagctccacg catcgcccac tccagaaaaa cagctgctgt agcggggatc    180
gcattgcaaa atcatctgcc ccagctccac atgcaggtcc ttatatttgt tttccatatc    240
agttaattca gtgactacat catttgcaag ctgttcgagc ttatccggat caactgcaat    300
gtttcctgac acaccgttca cctcccgagt ttatgtcttt cctctcttgc tttacgctcc    360
agttcttcca ttctggcaat ttcagctttt cgttcttcta ttttgacagc ggcagccttc    420
agctcttggc ttgtttcaag cagctcctgt tcgaattgat cgtaggcggc tttcgtttcc    480
tcgaaatcct ggtcaaacga atctcttgct ttgccctgcc aagcatctcc caatgcagat    540
aaccgggatt caagcagcat tttggagctt ctgacctctt ctgcggccgc actatacttg    600
tttgccagct caatgacttt atatgagtcc aacttttgtc ccctgccttt tctaaattca    660
cgcacaattg gatgtttttat ataaatgatt ataaataatt cggcatgtat ccgaatcgta    720
caaaagaacc ttttcataag aattggaagg gcgtatattc acttaaaatt cacagttggt    780
gagactttaa gattacaaaa aaggtaaaaa aaccaaatct ctcagacata aggcaaatga    840
gaaatttccc gctctatggg aaaaaacact aaagttgatc aaatgaccta agtgcgccaa    900
acgtgttacg ggacgagcta tctcatggta taaatggaat tgtaaac                 947

<210> SEQ ID NO 172
<211> LENGTH: 997
<212> TYPE: DNA
<213> ORGANISM: Bacillus amyloliquefaciens -continued

```
<400> SEQUENCE: 172
acgggtgctg caggaacgga aagtcacccc ggtcggcggg acaaaagaaa ttcccatcga      60
catcagaatc atcaccgccg cacacactga tctgagacag cttgtcgaaa gcaaaaagct     120
gagagaagat ttattttacc ggcttcacgt ctgtccgatt catcttccgc cattaagaga     180
acgcactgaa gacattcccg gcctcttctt tgaatttcag cgaaacagca ggtggccggg     240
agagcttcct gatgactttt tagacatatt aaagggctgg aaatggccgg ggaatatcag     300
agaattgttt aatgtgtttg aacgtctttc cgtcatgttc ccggacggac ggctgtccgg     360
acgtcccctc gcatccctgc ttgaagcgtc aggtcttaaa gaggcggccc agccttttga     420
acaagaagaa gcgcctcctg tctctatacg ggagcacatt cagaaaaaca tgatcgtaaa     480
cgcgcttgaa tcggcgaagg gaaatgtcac gcaggccgcc aaaattgcgg ggattccgcg     540
tagcacgttt tacaaacgcc tcaaaaaatt caaactcacc gccggacaat tgtaagaaac     600
aagcatactt ctcttggctg ccggacacgt tatgtgtgag gcccaaagga ggtttgagac     660
gtgaatacac agcgtgcgaa agacattgct gaatccgccg ccatggcgta tgtgacgtat     720
gaaggagtcc cgatttatat tcagcatgtc aacgaagaca agaaacagc caggatttt      780 ccggtcggaa atcctcaatt tgagcaggaa gtgctgcttt ctgatttaca agagcatttt     840
tgagaaaagg tctgctgatc aaagcagacc ttttatgttc ctgtgagaac tttcccgctt     900
tttgagaaaa ataactaaaa atgattaaat gatctaactc ccccaaaccc ggtacagaga     960
agccgttctc atgatataaa taaaatgtaa acgttat                              997

<210> SEQ ID NO 173
<211> LENGTH: 20
<212> TYPE: DNA
<213> ORGANISM: Artificial
<220> FEATURE:
<223> OTHER INFORMATION: Primer

<400> SEQUENCE: 173
agtcacgacg ttgtaaaacg                                                  20

<210> SEQ ID NO 174
<211> LENGTH: 20
<212> TYPE: DNA
<213> ORGANISM: Artificial
<220> FEATURE:
<223> OTHER INFORMATION: Primer

<400> SEQUENCE: 174
tgttgtgtgg aattgtgagc                                                  20

<210> SEQ ID NO 175
<211> LENGTH: 881
<212> TYPE: DNA
<213> ORGANISM: Bacillus subtilis

<400> SEQUENCE: 175
gcatgcaaaa aatcaaataa ggagtgtcaa gaatgaggtt taataataaa atgttggcct      60
tggcagcact acttttttgca gcgcaagcgt cagcagacac gctcgaatca atagacaatt    120
gcgcggtcgg atgtccaaca ggaggcagta gcaatgtctc tattgtcaga catgcttata    180
cgttgaataa taacagtaca acaaagtttg ccaattgggt tgcatatcat attacaaaag    240
acacgccagc aagcggaaag acaagaaatt ggaaaacaga tcctgctctc aatcctgcgg    300
acactcttgc gcctgctgat tacacaggtg ccaatgccgc gcttaaagtc gatcgaggtc    360
```

```
atcaagcgcc tcttgcatct cttgcgggag tttccgactg ggaatcgttg aactacctttt     420 caaacatcac gccacaaaag tcagatttaa accagggagc ttgggctcgg ctggaagatc      480
aggaacgtaa attaattgat cgtgctgata tctcatcggt gtatactgtt accgggccgc      540
tgtatgagag agatatgggc aaattacctg gcactcagaa agcgcacacc atcccagcg       600 cctactggaa ggtaattttt attaacaaca gcccggcggt taaccactat gcagcatttc     660
ttttcgacca gaacacgccg aagggcgccg atttctgtca atttcgcgtg acggtggacg     720
agatcgagaa aaggacagga ctgattatct gggccggtct gccggacgac gtgcaggctt     780
ctctgaagag caaaccgggc gttctgccgg agttgatggg ctgcaaaaac tgacgaaaaa     840
acccgccgaa gcgggtttat tcttcacgcg ggcgcctgca g                         881
```

<210> SEQ ID NO 176
<211> LENGTH: 1066
<212> TYPE: DNA
<213> ORGANISM: Artificial
<220> FEATURE:
<223> OTHER INFORMATION: kuenstliche Nukleasesequenz inklusive
      Signalpeptid und Ribosomenbindungsstelle

<400> SEQUENCE: 176

```
agtcacgacg ttgtaaaacg acggccagtg aattcgagct cggtacctcg cgaatgcatc      60
tagatccaat gcatgcaaaa aatcaaataa ggagtgtcaa gaatgaggtt taataataaa     120
atgttggcct tggcagcact acttttttgca gcgcaagcgt cagcagacac gctcgaatca    180
atagacaatt gcgcggtcgg atgtccaaca ggaggcagta gcaatgtctc tattgtcaga    240
catgcttata cgttgaataa taacagtaca acaaagtttg ccaattgggt tgcatatcat    300
attacaaaag acacgccagc aagcggaaag acaagaaatt ggaaaacaga tcctgctctc    360
aatcctgcgg acactcttgc gcctgctgat tacacaggtg ccaatgccgc gcttaaagtc    420
gatcgaggtc atcaagcgcc tcttgcatct cttgcgggag tttccgactg ggaatcgttg    480 aactacctttt caaacatcac gccacaaaag tcagatttaa accagggagc ttgggctcgg   540
ctggaagatc aggaacgtaa attaattgat cgtgctgata tctcatcggt gtatactgtt    600
accgggccgc tgtatgagag agatatgggc aaattacctg gcactcagaa agcgcacacc    660 atcccagcg cctactggaa ggtaattttt attaacaaca gcccggcggt taaccactat     720
gcagcatttc ttttcgacca gaacacgccg aagggcgccg atttctgtca atttcgcgtg    780
acggtggacg agatcgagaa aaggacagga ctgattatct gggccggtct gccggacgac    840
gtgcaggctt ctctgaagag caaaccgggc gttctgccgg agttgatggg ctgcaaaaac    900
tgacgaaaaa acccgccgaa gcgggtttat tcttcacgcg ggcgcctgca gattggatcg   960
gatcccgggc ccgtcgactg cagaggcctg catgcaagct tggcgtaatc atggtcatag  1020
ctgtttcctg tgtgaaattg ttatccgctc acaattccac acaaca                 1066
```

<210> SEQ ID NO 177
<211> LENGTH: 147
<212> TYPE: DNA
<213> ORGANISM: Artificial
<220> FEATURE:
<223> OTHER INFORMATION: Multiple Klonierungsstelle (Multicloning-site)

<400> SEQUENCE: 177

```
ggatcgatcc gcatgcgagc tcggtacccc gggtcgacct gcagccaagc ttaattagct      60
gagcttggac tcctgttgat agatccagta atgacctcag aactccatct ggatttgttc    120
```
agaacgctcg gttgccgccg ggcgttt                                           147

<210> SEQ ID NO 178
<211> LENGTH: 28
<212> TYPE: DNA
<213> ORGANISM: Artificial
<220> FEATURE:
<223> OTHER INFORMATION: Primer

<400> SEQUENCE: 178
cgccaaacgt gttacgggac gagctatc                                           28

<210> SEQ ID NO 179
<211> LENGTH: 26
<212> TYPE: DNA
<213> ORGANISM: Artificial
<220> FEATURE:
<223> OTHER INFORMATION: Primer

<400> SEQUENCE: 179
aaacgcccgg cggcaaccga gcgttc                                             26

<210> SEQ ID NO 180
<211> LENGTH: 1047
<212> TYPE: DNA
<213> ORGANISM: Artificial
<220> FEATURE:
<223> OTHER INFORMATION: kuenstliche Nuklesasesequenz

<400> SEQUENCE: 180
cgccaaacgt gttacgggac gagctatctc atggtataaa tggaattgta aacggatcga        60
tccgcatgca aaaatcaaa taaggagtgt caagaatgag gtttaataat aaaatgttgg       120
ccttggcagc actactttt gcagcgcaag cgtcagcaga cacgctcgaa tcaatagaca       180
attgcgcggt cggatgtcca acaggaggca gtagcaatgt ctctattgtc agacatgctt      240
atacgttgaa taataacagt acaacaaagt ttgccaattg ggttgcatat catattacaa      300 aagcacgcc agcaagcgga aagacaagaa attggaaaac agatcctgct ctcaatcctg       360
cggacactct tgcgcctgct gattacacag gtgccaatgc cgcgcttaaa gtcgatcgag       420
gtcatcaagc gcctcttgca tctcttgcgg gagtttccga ctgggaatcg ttgaactacc      480
tttcaaacat cacgccacaa aagtcagatt taaaccaggg agcttgggct cggctggaag      540
atcaggaacg taaattaatt gatcgtgctg atatctcatc ggtgtatact gttaccgggc      600
cgctgtatga gagagatatg ggcaaattac ctggcactca gaaagcgcac accatacca       660 gcgcctactg gaaggtaatt tttattaaca acagcccggc ggttaaccac tatgcagcat      720
ttcttttcga ccagaacacg ccgaagggcg ccgatttctg tcaatttcgc gtgacggtgg      780
acgagatcga gaaaggaca ggactgatta tctgggccgg tctgccggac gacgtgcagg       840
cttctctgaa gagcaaaccg ggcgttctgc cggagttgat gggctgcaaa aactgacgaa      900
aaaacccgcc gaagcgggtt tattcttcac gcgggcgcct gcagccaagc ttaattagct      960
gagcttggac tcctgttgat agatccagta atgacctcag aactccatct ggatttgttc     1020
agaacgctcg gttgccgccg ggcgttt                                          1047

<210> SEQ ID NO 181
<211> LENGTH: 137
<212> TYPE: DNA
<213> ORGANISM: Artificial
<220> FEATURE:

<223> OTHER INFORMATION: Multiple Klonierungsstelle (Multicloning-site)

<400> SEQUENCE: 181

```
gcatgcgagc tcggtacccc gggtcgacct gcagccaagc ttaattagct gagcttggac      60
tcctgttgat agatccagta atgacctcag aactccatct ggatttgttc agaacgctcg     120
gttgccgccg ggcgttt                                                   137
```

<210> SEQ ID NO 182
<211> LENGTH: 50
<212> TYPE: DNA
<213> ORGANISM: Artificial
<220> FEATURE:
<223> OTHER INFORMATION: Primer

<400> SEQUENCE: 182

```
ggttctggca ggaccggcgg ctgcgtcagc agacacgctc gaatcaatag                 50
```

<210> SEQ ID NO 183
<211> LENGTH: 25
<212> TYPE: DNA
<213> ORGANISM: Artificial
<220> FEATURE:
<223> OTHER INFORMATION: Primer

<400> SEQUENCE: 183

```
cgcagccgcc ggtcctgcca gaacc                                            25
```

<210> SEQ ID NO 184
<211> LENGTH: 176
<212> TYPE: DNA
<213> ORGANISM: Artificial
<220> FEATURE:
<223> OTHER INFORMATION: kuenstliche Sekretionssequenz

<400> SEQUENCE: 184

```
cgccaaacgt gttacgggac gagctatctc atggtataaa tggaattgta acggatccg       60 catgcaaata aggagtgtca agaatgtttg caaaacgatt caaaacctct ttactgccgt     120
tattcgctgg attttattg ctgtttcatt tggttctggc aggaccggcg gctgcg          176
```

<210> SEQ ID NO 185
<211> LENGTH: 85
<212> TYPE: DNA
<213> ORGANISM: Artificial
<220> FEATURE:
<223> OTHER INFORMATION: Primer

<400> SEQUENCE: 185

```
ggttctggca ggaccggcgg ctgcgtcagc agaccaccat caccatcacc atggcggcga      60
cacgctcgaa tcaatagaca attgc                                            85
```

<210> SEQ ID NO 186
<211> LENGTH: 9
<212> TYPE: PRT
<213> ORGANISM: Artificial
<220> FEATURE:
<223> OTHER INFORMATION: Primer

<400> SEQUENCE: 186

```
Gly Gly His His His His His His His
1               5
```

<210> SEQ ID NO 187

```
<211> LENGTH: 9
<212> TYPE: PRT
<213> ORGANISM: Artificial
<220> FEATURE:
<223> OTHER INFORMATION: Primer

<400> SEQUENCE: 187

Asp His His His His His His Gly Gly
1               5
```

METHOD FOR PRODUCING SERRATIA MARCESCENS NUCLEASE USING A BACILLUS EXPRESSION HOST

CROSS REFERENCE TO RELATED APPLICATIONS

This application is a continuation of international patent application no. PCT/EP2010/004709, filed Aug. 2, 2010, designating the United States of America, and published in German on Feb. 10, 2011 as WO 2011/015327, the entire disclosure of which is incorporated herein by reference. Priority is claimed based on European patent application no. EP 09 009 992.0, filed Aug. 3, 2009, the entire disclosure of which is likewise incorporated herein by reference.

The instant application contains a Sequence Listing which has been submitted via EFS-web and is hereby incorporated by reference in its entirety.

BACKGROUND OF THE INVENTION

The invention relates to a method for producing a nuclease of a Gram-negative bacterium or a nuclease preparation containing a nuclease of a Gram-negative bacterium comprising the expression of the nuclease in a Gram-positive bacterium and the subsequent secretion of the nuclease.

Nucleases are hydrolytic enzymes that split nucleic acids and are of widespread economic importance. Specific nucleases such as restriction enzymes are distinguished here from non-specific nucleases such as RNase A. Restriction enzymes have become indispensable tools in molecular biology and serve to specifically split different DNA molecules, which are joined together using ligases to form new constructs. Non-specific nucleases are mainly used for the decomposition of nucleic acids in various processes. When the nuclease cleaves only DNA, this is referred to as a "DNase", and when the nuclease cleaves only RNA, this is referred to as an "RNase". A typical representative of DNases is DNase I from the pancreas of mammals. Typical representatives of RNases are, for example, RNase T1 and T2 from *Aspergillus oryzae* or RNase A also from the pancreas of mammals.

Besides the application for removing RNA from DNA samples by treating with RNases or removing DNA from RNA samples by treating with DNases, further applications of significant economic interest are those in which both DNA and RNA are removed from the sample. This relates, for example, to the production of a wide variety of molecules by cell-based or cell-free biological systems, in which the product is not composed of nucleic acids, as in the case of proteins such as antibodies or enzymes, polysaccharides, lipids, for example, or low-molecular substances such as antibiotics, metabolic end products or intermediate products or chemicals. The necessity to remove the nucleic acids becomes particularly significant if production of the molecules occurs intracellularly or if a proportion of the production cells is lysed during production. As a result of this, during preparation of the molecules large amounts of nucleic acids are also released or are contained in the preparation which contaminate the desired molecule or make further purification thereof more difficult. A similar problem results, for example, in the production of proteins using cell-free in-vitro translation. The purification is made difficult, amongst other factors, by the nucleic acids increasing the viscosity of the preparations to such an extent that subsequent steps such as filtration or chromatography operations are not possible.

Hence, there is great interest in such processes to remove the contaminating nucleic acids or to digest these to such an extent that no further restriction to the further process steps occurs. One possibility of removing the nucleic acids consists in the specific precipitation of the nucleic acids by different agents. Another possibility consists in breaking down the nucleic acids to such small fragments using nucleases that the viscosity of the samples is reduced and the resulting decomposition products can be separated using simple methods such as e.g. ultrafiltration.

The use of nucleases that can cleave both RNA and DNA is particularly advantageous for an application for removal of all nucleic acids, i.e. both RNA and DNA, from different samples. In this case, the nuclease used should have a high activity and sufficient stability. A nuclease that exhibits these properties is the nuclease from the Gram-negative bacterium *Serratia marcescens* [EC 3.1.30.2; SEQ ID 1, Filimonova M N, Balaban N P, Sharipova F P, Leshchinskaia I B, Biokhimiia, 1980, 45(11): 2096-104; Filimonova M N, Baratova L A, Vospel'nikova N D, Zheltova A O, Leshchinskaia I B, Biokhimiia, 1981, 46(9): 1660-6; Ball T K, Saurugger P N, Benedik M J, Gene. 1987, 57(2-3): 183-92; Biedermann K, Jepsen P K, Riise E, Svendsen I, Carlsberg Res Commun. 1989, 54(1): 17-27]. This enzyme is also distributed under the brand name Benzonase and is referred to below as "*Serratia marcescens* nuclease".

To be able to produce proteins economically in sufficient quantities and with the required purity, they are frequently produced using standard expression organisms by heterologous expression, i.e. the genetic information for the desired protein is incorporated into the expression organism, which then undertakes the expression, i.e. synthesis, of the protein foreign to it. This frequently has the advantage that the yield in these expression organisms can be increased very significantly compared to the original organism and established processes are available for cultivation of the expression organisms and their further treatment for product fabrication.

Nucleases can exert a high toxic potential on the host organism in the case of a disturbed or defective expression. If the nuclease already changes into an active form in the cytosol, it would split the nucleic acids of the host and cause them to die or inhibit their growth. Equally, a fault in folding or secretion can cause the secretion mechanism of the host to be blocked or impaired, which can also lead to death or growth inhibition.

The recombinant expression of the *Serratia marcescens* nuclease in the Gram-negative bacterium *Escherichia coli* is described in patent EP 229 866 B1 and described in comparison to the expression yield in the wild strain—*Serratia marcescens* W225. It is shown in Table 3 in page 13 and page 14 that with the system used a nuclease yield of 35 units/ml of culture was obtained with the recombinant *E. coli* strain and 7 units/ml with the wild strain. Moreover, it is disclosed that approximately half the activity remains in the periplasm of *E. coli* and is not secreted into the medium (Table 4 in EP 229 866 B1).

Biedermann K, Fiedler H, Larsen B S, Riise E, Emborg C, Jepsen P K, Appl. Environ. Microbiol. 1990, 56(6): 1833-8 also describe the secretion of a *Serratia marcescens* nuclease (from the *Serratia marcescens* strain W280) in *E. coli*. The study shows a comparison of the secretion rates of the nuclease in the homologous Gram-negative host organism *Serratia marcescens* and the likewise Gram-negative model organism *E. coli*. Nuclease yields per ml of culture under fermentation conditions that correspond to 16 500 units/ml are reported in the publication (Table 1, page 1837).

There are also papers in the prior art that relate to the homologous expression of a ribonuclease in the Gram-positive host *Bacillus subtilis* (Nakamura A, Koide Y, Miyazaki H, Kitamura A, Masaki H, Beppu T, Uozumi T, Eur. J. Biochem. 1992, 209(1): 121-127). Secretion yields of 7.2 units/ml are reported.

An expression of a heterologous nuclease in a Gram-positive bacterium is also described in the prior art (Dieye Y, Usai S, Clier A, Gruss A, Piard J-C, J. Bact. 2001, 183(14): 4157-4166). In this study the nuclease from the Gram-positive bacterium *Staphylococcus aureus* is expressed in the Gram-positive bacterium *Lactobacillus lactis*. The aim of this study is in particular to establish a system for the expression of desired proteins in the intestine of humans or animals by *L. lactis* (page 4157, left column).

The Gram staining is an important criterion for the differentiation of bacteria according to the structure of their cell wall. It is based on the different structure of the bacterial envelope composed of different peptidoglycans as well as teichoic acids. Gram-positive bacteria in this case have a thicker multilayer murein envelope that can represent up to almost 50% of the envelope dry mass. In addition, the cell wall contains between 20% and 40% teichoic acids. In contrast, Gram-negative bacteria have only a thin single-layer murein envelope, which only represents about 10% of the dry mass of the bacterial envelope and does not contain any teichoic acids. Methods for conducting the Gram staining are known to the person skilled in the art. Examples of Gram-negative bacteria are all types of the proteobacteria division such as enterobacteria (*Escherichia coli*, *Salmonella*, *Shigella*, *Klebsiella*, *Proteus*, *Enterobacter*) or *Pseudomonas*, *Legionella*, *Neisseria*, *Serratia marcescens*, the original host of the *Serratio marcescens* nuclease, is likewise a Gram-negative bacterium. Examples of Gram-positive bacteria are actinobacteria and strains of the Firmicutes (e.g. *Streptococcus*, *Enterococcus*, *Staphylococcus*, *Listeria*, *Bacillus*, *Clostridium*, *Lactobacillus*).

Gram-negative bacteria in general and *E. coli* in particular are distinguished by some disadvantages. On the one hand, secretion is often possible only in small yields and generally leads only into the periplasm and not directly into the medium, which makes possibly necessary subsequent purifications more difficult. On the other hand, Gram-negative bacteria often form endotoxins on a large scale. They are formed from a hydrophilic polysaccharide component and a lipophilic lipid component. In contrast to the bacteria they come from, endotoxins are highly heat-stable and even survive sterilisation. Endotoxins belong to the pyrogens, i.e. they can generate fever in humans and many types of animals upon contact with mucous membranes and passage into the bloodstream. Moreover, they activate a series of signalling pathways from immunocompetent cells that can either cause inflammation or a programmed cell death (apoptosis) of these cells. They are already biologically active in extremely low concentrations (lower pg/mL range).

Consequently, complex purification processes are necessary to reduce these endotoxins to below the biologically active concentration from samples, which can pass directly or indirectly into the human or animal bloodstream. This situation is particularly relevant for pharmaceutical applications.

SUMMARY OF THE INVENTION

Therefore, it is an object of the present invention to provide nucleases that have advantages compared to the prior art.

Another object of the invention is to provide nucleases in economically relevant quantities.

A further object of the invention is to provide a method of producing nucleases that reduces or even prevents the disadvantages of the prior art with respect to the production of nucleases.

These and other object of the invention are achieved by the invention as described and claimed hereinafter.

The invention thus relates to a method for producing a nuclease of a Gram-negative bacterium or for producing a nuclease preparation containing a nuclease of a Gram-negative bacterium comprising the expression of the nuclease in a Gram-positive bacterium and the subsequent secretion of the nuclease.

It has surprisingly been found that nucleases of a Gram-negative bacterium can be produced with high yields and high purity in Gram-positive bacteria by heterologous expression. In particular, it has been found that the *Serratia marcescens* nuclease can be efficiently expressed in *Bacillus* sp. by secretion.

The following Table collates the yields of expressed nuclease obtained in different hosts. (1) relates to the expression of the nuclease from the Gram-positive host *Bacillus subtilis* in the Gram-positive host *Bacillus subtilis* (Nakamura et al. Eur. J. Biochem. 209, 121-127 (1992)), (2) shows the best expression yield of the nuclease from the Gram-negative host *Serratia marcescens* in the Gram-negative host *Escherichia coli* (illustrative embodiment 7) and (3) shows the expression yield of the nuclease from the Gram-negative host *Serratia marcescens* in the Gram-positive host *Bacillus subtilis* (method according to the invention; plasmid construct 5 in illustrative embodiment 6):

| | 1 | 2 | 3 |
|---|---|---|---|
| Nuclease origin | Gram-positive | Gram-negative | Gram-negative |
| Expression host | Gram-positive | Gram-negative | Gram-positive |
| Yield | 7.5 U/ml | 74 U/ml (flask) 86 U/ml (fermenter) | 3700 U/ml |

It can be seen that an expression yield that is many times higher is achieved with the method according to the invention.

It is to be noted in this case that *Bacillus* sp. already exhibits the proliferation optimum at approximately 30° C., whereas *E. coli*, for example, exhibits such an optimum at approximately 37° C. This results, amongst other things, in advantages with respect to the amount of energy saved in large-scale production during fermentation.

It has surprisingly been found that nucleases or nuclease preparations that are distinguished by having no, or at most few, contaminants as result of endotoxins are obtainable by the method according to the invention. This provides particular advantages, since complex purification processes for separating endotoxins become unnecessary.

The term "endotoxins" is used for various substances in the prior art. Besides the meaning used within the framework of the present invention, specific substances from Gram-positive bacteria are also referred to individually as "endotoxin" in the prior art, e.g. the "delta endotoxin" from *Bacillus thuringiensis* or specific substances from *Listeria monocytogenes*.

However, in the meaning of the present invention the term preferably covers only toxins that occur in the outer membrane of specific Gram-negative bacteria or blue algae and that relate chemically to lipopolysaccharides (LPS).

Surprisingly, the expression and secretion occurs without the nuclease developing activities that disrupt the production process already in the cytosol or without damaging the secretion mechanism of the host such that inhibitions in growth or production or increased cell lysis occur.

As a result of the surprisingly successful expression of a nuclease of a Gram-negative bacterium in a Gram-positive bacterium, it is now possible to obtain the expressed and secreted nuclease directly from the medium. A lysis of cells, such as is generally necessary with Gram-negative bacteria as a result of the frequent inability of secretion into the medium, is not necessary within the framework of the inventive method.

Moreover, because of the completely differently structured cell envelope and the resulting different secretion mechanisms of the Gram-positive bacteria, further disadvantages can be avoided that can occur in the heterologous expression of proteins in Gram-negative bacteria. This includes, for example, the occurrence of inclusion bodies in Gram-negative cells that can be caused, inter alia, by an overload of the secretion systems of the Gram-negative bacterium as a result of a correspondingly high expression.

Nucleases in the sense of the present invention are preferably all enzymes that are assigned to the following EC classes of the International Union of Biochemistry and Molecular Biology: EC 3.1.11, EC 3.1.13, EC 3.1.14, EC 3.1.15, EC 3.1.16, EC 3.1.21, EC 3.1.25, EC 3.1.26, EC 3.1.27, EC 3.1.30, EC 3.1.31.

Nucleases can cleave DNA or RNA or both. In this case "DNase" is understood to mean any DNA-cleaving activity and "RNase" any RNA-cleaving activity.

In one preferred embodiment the nuclease is a pure DNase without RNase activity.

In another preferred embodiment the nuclease is a pure RNase without DNase activity.

In a further preferred embodiment the nuclease exhibits both DNase and RNase activity.

Therefore, enzymes assigned to the EC classes 3.1.21.1, 3.1.21.2, 3.1.21.5, 3.1.22.5, 3.1.26, 3.1.27 are particularly preferred.

Enzymes assigned to EC class 3.1.30 and 3.1.31, in particular EC class 3.1.30.2, are most particularly preferred.

Most preferred are enzymes characterized by the accession numbers of Swiss-Prot or TrEMBL: P13717, A1JRS9, A8GCS3, Q15YD6, Q4HET4, Q0P9S3, B9D1S3, Q4HQP0, Q4HP86, Q4SK4, B7LWY5, B7LJ21, B7LJB7, B7LIP6, A4G9G4, A7JPX5, Q3JB45, Q3JBS7, A8R779, P29769, Q5LPJ4.

The term "nuclease" preferably covers a protein that is characterized by an amino acid sequence, which has a homology of at least 60%, preferably at least 70%, particular preferred at least 80%, most particularly preferred at least 90% to a native nuclease, and which additionally exhibits nuclease activity.

In the sense of the invention "nuclease activity" preferably means that the protein can cut DNA or RNA or DNA and RNA to form oligonucleotides or mononucleotides. This cutting preferably occurs in aqueous solutions at an incubation temperature of −20° to 60° C. and a breakdown of high-molecular, acid-insoluble DNA and/or RNA into low-molecular, acid-soluble oligo- and/or mononucleotides occurs.

Particularly preferred are proteins that exhibit a specific nuclease activity that is 5% higher than the specific activity of the native nuclease, to which they have a corresponding homology. Specific activity in this case is the catalytic activity of a defined amount of protein of the nuclease.

Particularly preferred are modifications, which preferably lead to more than 10%, more preferred more than 20%, further preferred more than 50% and most preferred more than 100% increase in the specific activity of the wild-type nuclease.

It is particularly preferred if DNA sequences encoding the nucleases are used that are codon-optimized with respect to the Gram-positive bacterium, which can be achieved by using optimal base triplets for the corresponding amino acid.

In the sense of the invention homology of a sequence is preferably calculated as identity using BLASTP 2.2.20+ (Stephen F. Altschul, Thomas L. Madden, Alejandro A. Schäffer, Jinghui Zhang, Zheng Zhang, Webb Miller and David J. Lipman (1997), "Gapped BLAST and PSI-BLAST: a new generation of protein database search programs", Nucleic Acids Res. 25:3389-3402; Stephen F. Altschul, John C. Wootton, E. Michael Gertz, Richa Agarwala, Aleksandr Morgulis, Alejandro A. Schäffer and Yi-Kuo Yu (2005).

The nuclease preferably has a homology of at least 60% to SEQ_ID_3, which represents the amino acid sequence of the *S. marcescens* nuclease.

Overall, nucleases retain only little among themselves. Thus, the aforementioned nuclease of the Gram-positive bacterium *Staphylococcus aureus* has at most a low homology to the nuclease of the Gram-negative bacterium *Serratia marcescens*.

In the sense of the present invention, the term "nuclease of a Gram-negative bacterium" is preferably defined exclusively via the primary sequence of the mature nuclease or the DNA sequence of the corresponding wild-type bacterium encoding this primary sequence. If the expression in the Gram-positive bacterium should lead to post-translational modifications of the nuclease that do not occur in Gram-negative bacteria, or vice versa, then it is still a nuclease of a Gram-negative bacterium in the sense of the description.

What are preferably not included in the term "nuclease of a Gram-negative bacterium" in the sense of the invention are amino acid sequences that are firstly likewise expressed as part of the expression of the gene encoding the nuclease, but are not part of the mature nuclease. These amino acid sequences not encompassed by the term include secretion sequences, for example. Secretion sequences are also known to the skilled person as signal peptides.

The meaning of the term "Gram-negative bacteria" in the sense of the present invention is the same as the meaning of the term in the prior art. Gram-negative bacteria, which preferably serve as a source for nucleases and are therefore preferred Gram-negative bacteria in the sense of the present invention, are preferably all bacteria of the classes of proteobacteria such as alpha-proteobacteria, beta-proteobacteria, gamma-proteobacteria, delta-proteobacteria, epsilon-proteobacteria.

Particularly preferred are bacteria of all orders of gamma-proteobacteria such as Acidithiobacillales, Aeromonadales, Alteromonadales, Cardiobacteriales, Chromatiales, Enterbacteriales, Legionellales, Methylococcales, Oceanospirillales, Pasteurellales, Pseudomonadales, Thiotrichales, Vibrionales, Xanthomonadales.

Preferred species of the Enterobacteriales are *Arsenophonus, Brenneria, Buchnera, Budvicia, Buttiauxella, Cedecea, Citrobacter, Dickeya, Edwardsiella, Enterobacter, Erwinia, Escherichia, Ewingella, Hafnia, Klebsiella, Kluyvera, Leclercia, Leminorella, Moellerella, Marganella, Obesumbacterium, Pantoea, Pectobacterium, Photorhabdus, Plesiomonas, Pragia, Proteus, Providencia, Rahnella, Raoultella, Saccharobacter, Salmonella, Samsonia, Serratia, Shigella,*

Sodalis, Tatumella, Thorsellia, Trabulsiella, Wigglesworthia, Xenorhabdus, Yersinia, Yokenella.

Bacteria of the species *Serratia* such as *S. entomophila, S. ficaria, S. fonticola, S. grimesii, S. liquefaciens, S. odorifera, S. plymuthica, S. proteamaculans, S. quinivorans, S. rubidaea, S. ureilytica* are highly preferred. The type *Serratia marcescens* is most preferred.

The meaning of the term "Gram-positive bacteria" in the sense of the present invention is the same as the meaning of the term in the prior art.

Preferred Gram-positive bacteria in the sense of the present invention are bacteria of all strains of Actinobacteria and Firmicutes. Bacteria of the classes Bacilli, Clostridia and Mollicutes are particularly preferred in this case, and of these those preferred are bacteria of the Lactobacillales with the families Aerococcaceae, Carnobacteriaceae, Enterococcaceae, Lactobacillaceae, Leuconostocaceae, Oscillospiraceae, Streptococcaceae and the Bacillales with the families Alicyclobacellaceae, Bacillaceae, Caryophanaceae, Listeriaceae, Paenibacillaceae, Planococcaceae, Sporolactobacillaceae, Staphylococcaceae, Thermoactinomycetaceae, Turicibacteraceae.

Those most particularly preferred are bacteria belonging to the species of the family Bacillaceae such as *Alkalibacillus, Amphibacillus, Anoxybacillus, Bacillus, Caldalkalibacillus, Cerasilbacillus, Exiguobacterium, Filobacillus, Geobacillus, Gracilibacillus, Halobacillus, Halolactibacillus, Jeotgalibacillus, Lentibacillus, Marinibacillus, Oceanobacillus, Ornithinibacillus, Paraliobacillus, Paucisalibacillus, Pontibacillus, Pontibacillus, Saccharococcus, Salibacillus, Salinibacillus, Tenuibacillus, Thalassobacillus, Ureibacillus, Virgibacillus*.

Most preferred are bacteria of the species *Bacillus* such as *B. acidiceler, B. acidicola, B. acidocaldarius, B. acidoterrestris, B. aeolius, B. aerius, B. aerophilus, B. agaradhaerens. B. agri, B. aidingensis, B. akibai, B. alcalophilus, B. algicola, B. alginolyticus, B. alkalidiazo-trophicus, B. alkalinitrilicus, B. alkalitelluris, B. altitudinis, B. alveayuensis, B. alvei, B. amylolyticus, B. aneurinilyticus, B. aneurinolyticus, B. anthracia, B. aquimaris, B. arenosi, B. arseniciselenatis, B. arsenicoselenatis, B. arsenicus, B. arvi, B. asahii, B. atrophaeus, B. aurantiacus, B. axarquiensis, B. azotofixans, B. azotoformans, B. badius, B. barbaricus, B. bataviensis, B. beijingensis, B. benzoevorans, B. bogoriensis, B. boroniphilus, B. borstelenis, B. butanolivorans, B. carboniphilus, B. cecembensis, B. cellulosilyticus, B. centrosporus, B. chagannorensis, B. chitinolyticus, B. chondroitinus, B. choshinensis, B. cibi, B. circulans, B. clarkii, B. clausii, B. coagulans, B. coahuilensis, B. cohnii, B. curdianolyticus, B. cycloheptanicus, B. decisifrondis, B. decolorationis, B. dipsosauri, B. drentensis, B. edaphicus, B. ehimensis, B. endophyticus, B. farraginis, B. fastidiosus, B. firmus, B. plexus, B. foraminis, B. fordii, B. formosus, B. fortis, B. fumarioli, B. funiculus, B. fusiformis, B. galactophilus, B. galactosidilyticus, B. gelatini, B. gibsonii, B. ginsengi, B. ginsengihumi, B. globisporus, B. globisporus subsp. globisporus, B. globisporus subsp. marinus, B. glucanolyticus, B. gordonae, B. halmapalus, B. haloalkaliphilus, B. halodenitrificans, B. halodurans, B. halophilus, B. hemicellulosilyticus, B. herbersteinensis, B. horikoshii, B. horti, B. hemi, B. hwajinpoensis, B. idriensis, B. indicus, B. infantis, B. infernus, B. insolitus, B. isabeliae, B. jeotgali, B. kaustophilus, B. kobensis, B. koreensis, B. kribbensis, B krulwichiae, B. laevolacticus, B. larvae, B. laterosporus, B. lautus, B. lehensis, B. lentimorbus, B. lentus, B. litoralis, B. luciferensis, B. macauensis, B. macerans, B. macquariensis, B. macyae, B. malacitensis, B. mannanilyticus, B. marinus, B. marisflavi, B. marismortui, B. massiliensis, B. methanolicus, B. migulanus, B. mojavensis, B. mucilaginosus, B. muralis, B. murimartini, B. mycoides, B. naganoensis, B. nealsonii, B. neidei. B, niabensis, B. niacini, B. novalis, B. odysseyi, B. okhensis, B. okuhidensis, B. oleronius, B. oshimensis, B. pabuli, B. pallidus, B. pallidus* (illeg.), *B. panaciterrae, B. pantothenticus, B. parabrevis, B. pasteurii, B. patagoniensis, B. peoriae, B. plakortidis, B. pocheonensis, B. polygoni, B. polymyxa, B. popilliae, B. pseudalcaliphilus, B. pseudofirmus, B. pseudomycoides, B. psychrodurans, B. psychrophilus, B. psychrosaccarolyticus, B. psychrotolerans, B. pulvifaciens, B. pycnus, B. qingdaonensis, B. reuszeri, B. runs, B. safensis, B. salarius, B. salexigens, B. saliphilus, B. schlegelii, B. selenatarsenatis, B. selenitrireducens, B. seohaeanensis, B. shackletonii, B. silvestris, B. simplex, B. siralis, B. smithii, B. soli, B. sonorensis, B. sphaericus, B. sporothermodurans, B. stearothermophilus, B. stratosphericus, B. subterraneus, B. subtilis subsp. spizizenii, B. subtilis subsp. subtilis, B. taeanensis, B. tequilensis, B. thermantarcticus, B. thermoaerophilus, B. thermoamylovorans, B. thermoantarcticus, B. thermocatenulatus, B. thermocloacae, B. thermodenitrificans, B. thermoglucosidasius, B. thermoleovorans, B. thermoruber, B. thermosphaericus, B. thiaminolyticus, B. thioparans, B. thuringiensis, B. tusciae, B. validus, B. vallismortis, B. vedderi, B. velezensis, B. vietnamensis, B. vireti, B. vulcani, B. wakoensis, B. weihenstephanensis*.

Those preferred in particular are the types *B. amyloliquefaciens, B. brevis, B. cereus, B. licheniformis, B. megaterium, B. pumilus, B. subtilis*.

Therefore, a method for producing a nuclease preparation containing a nuclease from *Serratia marcescens* is particularly preferred, or more preferred a nuclease from *Serratia marcescens*, comprising the expression of the nuclease in *Bacillus* sp. and the subsequent secretion of the nuclease, preferably using a heterologous secretion sequence.

Strains of *B.* sp. optimized for the secretion are preferably used according to the invention. Such strains are known to persons skilled in the art. Reference is made to WO 99/004019, WO 00/039323, WO 04/060909, for example, in this context.

In the sense of the invention the term "nuclease preparation" covers a composition containing a nuclease, which is obtainable using the method according to the invention. The term also covers in particular compositions that additionally contain the bacteria according to the invention or constituents thereof and compositions that are obtainable by purifying the protease produced according to the invention.

In a preferred embodiment the composition is liquid and/or solid and/or gel-like.

In a preferred embodiment a DNA segment containing a DNA sequence that encodes the nuclease and a DNA sequence that encodes a secretion sequence is incorporated into a Gram-positive bacterium.

For this, according to the invention, a further DNA sequence that encodes a signal peptide (the secretion sequence), which is recognised by the secretion mechanism of the production host and leads to a secretion of the nuclease, is given precedence within the DNA segment of the DNA sequence that encodes the mature nuclease.

Besides sequences for the mature nuclease, genes for nucleases from Gram-negative bacteria can also encode secretion sequences, which lead to a secretion of the nuclease into the periplasm of the original organism or also to the surrounding medium. For example, the gene for the *Serratia marcescens* nuclease (SEQ-ID 1) has a sequence section that encodes the secretion sequence (SEQ-ID 2) and one that encodes the mature nuclease (SEQ-ID 3).

In a preferred embodiment, in the method according to the invention a DNA segment is incorporated into the host organism that contains a DNA sequence, which encodes the native secretion sequence, as well as a DNA sequence, which encodes the native protein sequence of the mature nuclease or correspondingly homologous protein sequences. This native secretion sequence is referred to as "homologous".

In the sense of the invention the term "homologous" means that the secretion sequence is identical to sequences that are present in an individual wild-type bacterium and form a functional unit there together with the corresponding nuclease sequence, i.e. are expressed in a wild-type bacterium as a molecule with the nuclease.

In the sense of the invention the term "homology" that will be defined in another part of the description is to be distinguished therefrom.

In another preferred embodiment a DNA segment containing a DNA sequence, which encodes another non-native secretion sequence, is incorporated into the host organism. Such a non-native foreign secretion sequence is referred to as heterologous.

In the sense of the invention the term "heterologous", particularly when it relates to secretion sequences, preferably means that the secretion sequence is not identical to the native secretion sequence of the nuclease.

Heterologous secretion sequences can be naturally occurring secretion sequences or artificial secretion sequences. Naturally occurring secretion sequences are such that lead to the secretion of proteins in their respective original organisms.

In a further preferred embodiment the method according to the invention is characterized in that the secretion sequence is heterologous.

In a non-exclusive list these can be, for example, the secretion sequences for proteases and peptidases, amylases, glycoamylases, cellulases, lipases, esterases, arabinases, glucanases, chitosanases, lyases, xylanases, nucleases, phosphatases, transport and binding proteins, proteins related to flagella or phages/viruses in prokaryotes and eukaryotes.

In the sense of the invention the term "heterologous" means that the secretion sequence is not identical to sequences, which are present in an individual wild-type bacterium and form a functional unit there with the corresponding nuclease sequence, i.e. a heterologous secretion sequence can be the secretion sequence of another protein of the original organism of the nuclease, it can be a secretion sequence of another protein of any other organism or a artificial secretion sequence.

It is particularly preferred if heterologous secretion sequences from Gram-positive bacteria are used.

Artificial secretion sequences are such that do not occur in wild-type organisms. Such artificial secretion sequences are simple to produce for the skilled person on the basis of knowledge of the recognition mechanisms and/or comparisons of known secretion sequences. Assays are known from the prior art that can be used to examine the suitability of a synthetically produced sequence as secretion sequence.

The term "artificial secretion sequences" also covers in particular amino acid sequences that have a homology of 60%, preferably 70%, particularly preferred 80%, most particularly preferred 90%, to the protein sequences of native secretion sequences and effect the secretion of a nuclease in a Gram-positive bacterium in place of a native secretion sequence.

Particularly preferred are artificial secretion sequences that result in an increase in the secretion amount of the nuclease by at least 5%, preferably by at least 20%, particularly preferred at least 50%, most particularly preferred at least 100%, compared with the use of naturally occurring secretion sequences for the secretion of the nuclease.

It is particularly preferred to use a heterologous secretion sequence selected from the group of secretion sequences comprising Bacilli for the proteins encoded by the genes: abnA, amyE, appA, aprE, bglC, bglS, bpr, csn, dppE, epr, feuA, fhuD, flgB, flgC, flgE, flgK, flhO, flhP, fliD, fliK, fliL, ggt, glpQ, hag, htrA, lipA, lytD, mntA, mpr, msmE, nprE, nucB, oppA, opuAC, pbpA, pbpB, pbpC, pbpX, pel, pelB, penP, phoA, phoB, phoD, phy, pstS, qcrA, rbsB, sacB, tasA, vpr, wapA, wprA, xepA, xkdG, xkdK, xkdM, xlyA, xynA, xynD, ybdN, ybdO, ybfO, ybxl, ycdH, yclQ, ydaJ, ydhF, ydhT, yesO, yfiY, yfkN, yflE, yfmC, yfnl, yhcJ, yhcR, yhdW, yheN, yjcM, yfA, ykwD, ylqB, yncM, ynfF, yoaW, yocH, yodJ, yolA, yolB, ypjP, yqgS, yqgU, yqiX, yqxl, yrpD, yrpE, yrvJ1, yuaB, yurl, yusA, yusW, yvcE, yvfO, yvgO, yvpA, ywaD, yweA, ywoF, ywtD, ywtF, yxeB, yxiA, yxkC.

Further especially preferred is a secretion sequence selected from the group of SEQ-ID 4-170.

Particularly preferred is a heterologous secretion sequence selected from the secretion sequences for amyE from *B. subtilis* (SEQ-ID 5) or *B. amyloliquefaciens* (SEQ-ID 170).

According to the invention, the method is conducted by incorporating the genetic information for a homologous or heterologous secretion sequence and a nuclease of a Gram-negative bacterium into a Gram-positive bacterium and secretion of the nuclease by the Gram-positive organism.

It is advantageous if a Gram-positive bacterium is selected for the secretion of the nuclease of a Gram-negative bacterium that is distinguished by a low level of secreted proteases. Such a Gram-positive bacterium is referred to as low-protease.

In a preferred embodiment the Gram-positive bacterium is a low-protease host and/or *Bacillus* sp.

In the sense of the present invention the term "low-protease" means that it is a type or a natural isolate of a species of bacteria, which has less than 50%, more preferred less than 25%, most preferred less than 10% of the average protease level of a different type or a natural isolate of the same species.

It is likewise particularly preferred if a Gram-positive bacterium is selected for the secretion of the nuclease of a Gram-negative bacterium, in which the protease level has been reduced by synthetic modifications.

These modifications are preferably randomly incorporated into the selected Gram-positive bacterium. Methods for generating random mutations such as chemical, UV-induced, radiation-induced mutagenesis or similar methods are known to the person skilled in the art. After conducting the mutagenesis the clones obtained are screened for clones with reduced protease levels and the clones obtained are used for secretion of the nuclease.

It is particularly preferred if these modifications are incorporated into the selected Gram-positive bacterium in a targeted manner. In this case, the genes that encode secreted proteases are identified and completely or partially replaced or modified so that the corresponding protease is no longer secreted or is only secreted to a reduced level. Methods for modifying genomic sequences are known to the person skilled in the art. It is most preferred if multiple or many of the genes encoding secreted proteases are identified and completely or partially replaced or modified so that the corresponding proteases are no longer secreted or are secreted to a reduced level.

It is particularly preferred if a Gram-positive bacterium is selected for secretion of the nuclease of a Gram-negative bacterium, in which the neutral proteases (e.g. npr) and/or alkaline proteases (e.g. apr) and/or further proteases (e.g. epr, bpr, mpr) are completely or partially deleted.

It is most preferred if a *B. amyloliquefaciens, B. brevis, B. cereus, B. licheniformis, B. megaterium, B. pumilus* or *B. subtilis*-strain is selected for secretion of the nuclease of a Gram-negative bacterium, in which the protease(s) npr and/or apr and/or epr and/or bpr and/or mpr is/are completely or partially deleted.

The expression of genes is controlled by promoters. In this case, promoters are DNA sequences that serve as recognition sites for the RNA polymerases. Promoters can have further sequences for binding additional activating or inhibiting factors besides the actual binding site for the RNA polymerase, but can also have sequences that influence the promoter by forming secondary structures.

In the case of promoters a distinction is made between constitutive and inducible promoters. While constitutive promoters are read permanently, inducible promoters are switched on during the course of the production process by an additional signal. In this case, the signal can be generated by internal or external factors. An internal factor would be, for example, arrival at a specific growth phase of the organism, such as the transition from the logarithmic phase into the stationary phase of bacilli. An external factor would be, for example, the availability of a specific substrate source such as starch or proteins, for example, or the presence of a defined inducer such as tetracycline, maltose or IPTG (isopropyl-[beta]-D-thiogalactopyranoside), for example. External and internal factors can also have a inhibiting effect, that is that the reading of the promoter is suppressed under specific conditions or when a specific substance is present.

Promoters, which range from being suppressed to not being active at all during a specific phase, the early growth phase of the culture, and can be turned on to a strong expression in another phase, the production phase of the culture, are particularly suitable for the heterologous expression of proteins in general and potentially toxic enzymes such as nucleases in particular.

In a preferred embodiment, a native promoter from a Gram-positive bacterium, i.e. a promoter of a Gram-positive wild-type bacterium, is used for the method according to the invention.

In a preferred embodiment the expression is controlled by a constitutive promoter. An example of such a promoter is the β-glucanase promoter of *Bacillus amylolyquefaciens*.

In a preferred embodiment expression is controlled by an inducible promoter, which preferably under non-induced conditions exhibits 30% at most, preferably 10% at most, particularly preferred 5% at most, most particularly preferred 1% at most of its maximum expression performance.

In a preferred embodiment such an inducible promoter can be a growth phase-dependent promoter.

Particularly preferred in this case is a promoter selected from the group of promoters for the genes abnA, amyE, appA, aprE, bglC, bglS, bpr, csn, dppE, epr, feuA, fhuD, flgB, flgC, flgE, flgK, flhO, flhP, fliD, fliK, fliL, ggt, glpQ, hag, htrA, lipA, lytD, mntA, mpr, msmE, nucB, oppA, opuAC, pbpA, pbpB, pbpC, pbpX, pel, pelB, penP, phoA, phoB, phoD, phy, pstS, qcrA, rbsB, sacB, tasA, vpr, wapA, wprA, xepA, xkdG, xkdK, xkdM, xlyA, xynA, xynD, ybdN, ybdO, ybfO, ybxI, ycdH, yclQ, ydaJ, ydhF, ydhT, yesO, yfiY, AN, yflE, yfmC, yfnl, yhcJ, yhcR, yhdW, yheN, yjcM, yjfA, ykwD, ylqB, yncM, ynfF, yoaW, yocH, yodJ, yolJ, yolA, yolB, ypjP, yqgS, yqgU, yqiX, yqxl, yrpD, yrpE, yrvJ1, yuaB, yurI, yusA, yusW, yvcE, yvfO, yvgO, yvpA, ywaD, yweA, ywoF, ywtD, ywtF, yxeB, yxiA, yxkC from bacilli.

It is most particularly preferred if a promoter for npr from *Bacillus* sp. is used.

In a further preferred embodiment an inducible promoter is induced by an external signal.

It is particularly preferred in this case if a heat-inducible, a sucrose-inducible, a starch-inducible, a DNA damage-inducible, a stress-inducible, antibiotic-inducible, cold-inducible, xylose-inducible, IPTG-inducible, arabinose-inducible, alkali-inducible, acid-inducible, inositol-inducible promoter from bacilli is used.

It is most particularly preferred if a maltose-inducible promoter from *Bacillus* sp. is used, and is most preferred if the maltose promoter used is from *B. subtilis* (SEQ-ID 171) or the maltose promoter used is from *B. amyloliquefaciens* (SEQ-ID 172).

In another embodiment a promoter is used that is a variant of a native promoter used in the method according to the invention. Such a promoter is referred to as "promoter variant" within the framework of the invention.

In the sense of the invention promoter variants are variants, which have a homology of at least 50%, preferably at least 60%, more preferred at least 70%, particularly preferred at least 80%, most particularly preferred at least 90% to a native promoter used according to the invention and the expression performance of which is at least 20%, preferably at least 50%, particularly preferred at least 100%, more preferred at least 200%, most particularly preferred at least 300% higher than the expression performance of these native promoters.

For a plurality of applications of proteins and enzymes in general and nucleases in particular, it is advantageous if the proteins, enzymes and nucleases are present in high-purity form. Besides classic methods of protein purification, which are known to the person skilled in the art, purification of the proteins can be simplified if the target protein has an additional amino acid sequence (affinity tag) attached to it, which allows interaction with a specific material, and thus binds the target protein to this material, and contaminants or by-products can be removed by washing. Moreover, it is then particularly advantageous that the tagged amino acid sequence can be used to immobilise the target protein permanently on a support to enable it to be removed again later from the application.

In a preferred embodiment the nuclease additionally has an affinity tag. A fusion protein comprising secretion sequence, mature nuclease and affinity tag thus results.

In one embodiment the DNA sequence that encodes the affinity tag is attached to the 3' end of the DNA sequence that encodes the nuclease, so that the affinity tag is fused to the C terminal of the mature nuclease.

In another embodiment the DNA sequence that encodes the affinity tag is attached between the DNA sequence that encodes the secretion sequence and the 5' end of the DNA sequence encoding the nuclease, so that the affinity tag is fused to the N terminal of the mature nuclease.

In a preferred embodiment a spacer composed of amino acid esters is inserted between the affinity tag and the mature nuclease or between the mature nuclease and the affinity tag. A preferred spacer is one containing not more than 1000 amino acid esters, more preferred not more than 100 amino acid esters, further preferred not more than 20 amino acid esters, particularly preferred not more than 10 amino acid esters, most particularly preferred not more than 5 amino acid esters.

The spacer preferably contains the recognition sequence of a specific protease to be able to split off the affinity tag and the spacer itself or parts of the spacer again.

In a particularly preferred embodiment the affinity tag is selected from the group of amino acid sequences binding bivalent ions (e.g. His-tag), carbohydrate- or chitin-binding amino acid sequences (e.g. maltose-binding protein, cellulose-binding protein or chitin-binding protein) or streptavidin-binding amino acid sequences (e.g. Strep-tag).

The DNA sequence that encodes the nuclease can be present in the bacterium in different ways.

In a preferred embodiment the DNA segment containing this DNA sequence is integrated into an expression vector.

The expression preferably occurs via an expression vector. Various of these expression vectors are known to the person skilled in the art. In the sense of the description the term "vector" covers plasmids, bacteriophages, BACs (bacterial artificial chromosomes) and cosmids.

In a preferred embodiment of the method the expression vector comprises a gene that encodes an antibiotic resistance as selection marker. This resistance gene is preferably selected from the group comprising resistance genes to kanamycin, erythromycin, tetracycline, spectinomycin, chloramphenicol, streptomycin, neomycin.

In a further preferred embodiment of the method the expression vector comprises a gene that compensates an auxotrophy of the bacterium as selection marker. Host organisms that cannot synthesise specific essential substances independently and require at least one further DNA sequence, the selection marker, for complementation, are understood to be auxotrophic.

In a most particularly preferred embodiment the expression vector comprises one or more copies of the glyA gene as selection marker and is used in a host organism, in which the glyA gene has been deleted or has been modified to have a reduced expression performance.

The expression of the nuclease preferably occurs via a plasmid. Plasmids are understood to be autonomously replicating DNA molecules that are extrachromosomal and do not belong to the bacterial chromosome. The size of the plasmid is 2 to 500 kbp, more preferred 3 to 100 kbp, further preferred 4 to 20 kbp, most particularly preferred 5 to 10 kbp.

In a particularly preferred embodiment of the method the plasmid is present in the host cell in more than one copy, preferably in more than 5 copies, further preferred in more than 10 copies, particularly preferred in more than 20 copies.

A replica of the plasmid is preferably selected that after 100 generations of cultivation without selection pressure still ensures the presence of the plasmid in at least 20%, more preferred 50%, further preferred at least 70%, particularly preferred at least 90% of the bacterial cells.

In another preferred embodiment the DNA segment containing the DNA sequence for expression of the nuclease is integrated into the bacterial chromosome.

It is preferred if at least 1 copy of the DNA segment containing this DNA sequence, more preferred at least 3 copies, further preferred at least 5 copies, particularly preferred at least 10 copies of this DNA segment is/are integrated into the bacterial chromosome.

In a preferred embodiment of the method a gene that encodes an antibiotic resistance is integrated into the bacterial chromosome as selection marker together with the DNA sequence that encodes the nuclease. This resistance gene is preferably selected from the group comprising resistance genes to kanamycin, erythromycin, tetracycline, spectinomycin, chloramphenicol, streptomycin, neomycin.

In a further preferred embodiment of the method a gene that compensates auxotrophy of the bacterium is integrated into the bacterial chromosome as selection marker together with the DNA sequence that encodes the nuclease. Host organisms that cannot synthesise specific essential substances independently and require at least one further DNA sequence, the selection marker, for complementation, are understood to be auxotrophic. This selection marker is preferably glyA.

In a further preferred embodiment of the method no selection marker at all is used on the expression vector or the integrated DNA segment containing the DNA sequence that encodes the nuclease, or the previously used selection marker is subsequently removed again so that a selection marker-free host strain is formed.

The invention additionally includes a Gram-positive bacterium containing a nuclease of a Gram-negative bacterium and/or a DNA sequence that encodes a nuclease of a Gram-negative bacterium.

In a preferred embodiment this DNA sequence is integrated into an expression vector, preferably a plasmid.

In another preferred embodiment the DNA sequence is integrated into the bacterial chromosome.

In a preferred embodiment of the method all media components of the Gram-positive host are selected for expression of the nuclease of a Gram-negative bacterium from non-animal sources.

In a preferred embodiment of the method the Gram-positive host for expression of the nuclease of a Gram-negative bacterium is cultivated using a fed-batch protocol. In this case fed-batch is understood to mean that a portion of the nutrients is already present at the beginning of the cultivation and a further portion of the nutrients is added continuously or discontinuously from a specific point in time.

In a further preferred embodiment a carbon source, a nitrogen source and a phosphate source as well as mixtures composed of required salts and trace elements and possibly essential amino acids and selection markers are present in the fed-batch protocol.

In a preferred embodiment of the method the Gram-positive host for expression of the nuclease of a Gram-negative bacterium is cultivated using a batch protocol. In this case batch is understood to mean that all the nutrients are already present at the beginning of cultivation and no further nutrients are added during cultivation. Solutions for correcting pH value or foam formation such as acids, alkaline solutions or anti-foaming agents do not apply as nutrients.

In a further preferred embodiment of the method the carbon source is preferably added in a concentration of more than 1% by weight per unit volume, more preferred more than 3%, further preferred more than 6% and particularly preferred more than 9%.

In a preferred embodiment of the method glucose is used as carbon source.

In another preferred embodiment of the method a dextrin is used as carbon source.

In yet another preferred embodiment of the method maltose is used as carbon source.

In a further preferred embodiment of the method the carbon source is converted to maltose or a mixture of maltose and another carbon source during cultivation.

In a still further preferred embodiment of the method hydrolysed peptone, particularly preferred hydrolysed soy peptone, is added to the cultivation.

In a further preferred embodiment of the method TRIS (tris(hydroxymethyl)-aminomethane) is added to the cultivation medium.

The method according to the invention leads to a high yield of nuclease.

In a preferred embodiment of the method according to the invention a yield of at least 5 000, more preferred at least 15 000, further preferred at least 25 000, particularly preferred at least 50 000, most particularly preferred at least 100 000 nuclease units per ml of culture medium is achieved.

In view of the existing requirement for endotoxin-free nucleases, there have been considerable efforts made hitherto to develop purification steps that serve to separate endotoxins from nucleases or nuclease preparations.

An overview of various methods for the removal of endotoxins, on which such a purification step can be based, is to be found in Magalhaes et al., (2007) J. Pharm. Phamaceut. Sci. 10: 388-404.

Purification steps for separating endotoxins known from the prior art are based on the following methods, for example: anion exchange chromatography; affinity chromatography; ion exchange chromatography, in particular ion exchange chromatography using alkanediol; ultrafiltration; purification using affinity adsorbents such as e.g. L-histidine, poly-L-histidine, poly(gamma-methyl L-glutamate), polymyxin B; gel filtration; gel filtration chromatography; sucrose gradient centrifugation; purification using dual-phase micelle systems; triton X-114-based phase separation; temperature-induced phase separation; purification by a non-selective adsorption with hydrophobic adsorbents or anion exchangers; polyacrylamide gel electrophoresis, in particular slab polyacrylamide gel electrophoresis; SDS gel electrophoresis; membrane-based chromatography; agarose gel electrophoresis; caesium chloride gradient centrifugation; affinity purification using beads.

The application of these methods in practice is associated in part with a significant expenditure and/or with various technical difficulties.

Since the method according to the invention is based on use of Gram-positive and not Gram-negative bacteria, contamination of the process product by endotoxins can be avoided.

In a further preferred embodiment the method according to the invention does not include a purification step that serves for the targeted separation of endotoxins.

Therefore, processes according to the invention are included in particular that do not include such purification steps based on the methods mentioned above or described in above-listed documents for the purposes of endotoxin removal or derived therefrom.

However, the method according to the invention can certainly comprise purification steps that are usual for enzyme preparations. However, these purification steps are preferably not directed towards the targeted separation of endotoxins.

A further aspect of the invention relates to a nuclease that is obtainable by the method according to the invention.

A further aspect of the invention relates to a nuclease preparation, which is obtainable by the method according to the invention, in particular by the preferred embodiment of the method according to the invention that does not include a purification step that serves for the targeted separation of endotoxins.

The nuclease preparation according to the invention contains the nuclease and possibly other ingredients. Thus, the nuclease preparation according to the invention can include in particular Gram-positive bacteria or components or constituents of Gram-positive bacteria, which remain in the preparation during the course of the purification of the nuclease by conventional purification steps. These components or constituents can be carbohydrates, fats, nucleic acids or proteins, or parts or fragments of these molecules. The constituents can also be composed of characteristic metabolites or secondary metabolites or be derived from these. The components and constituents can usually be identified using methods known to the person skilled in the art. Thus, nucleic acids, for example, can be amplified by PCR and identified by sequencing. Metabolic metabolites, for example, can be determined by HPLC or GC analytical methods. Further methods for the identification of Gram-positive cell constituents or debris are mass spectroscopy and also IR, NMR and UV/VIS spectroscopy.

In the sense of the invention the term "constituents of Gram-positive bacteria" or "constituents of a Gram-positive bacterium" preferably describes metabolites or secondary metabolites of the Gram-positive bacteria.

In the sense of the invention the term "components of Gram-positive bacteria" or "components of a Gram-positive bacterium" preferably describes molecules that are encoded in the native genome of the bacterium as well as parts of the native genome itself, and it therefore includes proteins, peptides, RNA and DNA molecules.

The composition preferably contains components of a Gram-positive bacterium.

The molecular proportion of the components of Gram-positive bacteria can amount to more than $10^{-10}$ mol % of the total amount of the composition, more preferred more than $10^{-8}$ mol % of the total amount of the composition, further preferred more than $10^{-6}$ mol % of the total amount of the composition, most preferred more than $10^{-4}$ mol % of the total amount of the composition.

The constituents and/or components of the Gram-positive bacterium originate at least partially from the Gram-positive bacterium/bacteria that have been used for expression of the nuclease.

The nuclease preparation can be solid, e.g. a lyophilised powder, paste-like or liquid, e.g. an aqueous solution or dispersion.

A nuclease preparation according to the invention preferably has less than 250 endotoxin units (EU) per mega unit (MU) of nuclease activity, more preferred less than 125 endotoxin units per MU of nuclease activity, more preferred less than 25 endotoxin units per MU of nuclease activity, particularly preferred less than 5 endotoxin units per MU of nuclease activity, most particularly preferred less than 1 endotoxin units per MU of nuclease activity.

In the sense of the present invention 1 unit of nuclease activity is defined as the quantity of enzymes that releases acid-soluble oligonucleotides from high-molecular DNA or RNA in 1 hour at 37° C., which corresponds to an absorption of 1 absorption unit at 260 nm. The abbreviation U corresponds to one unit, the abbreviation kU stands for a thousand units and the abbreviation MU stands for a mega unit, i.e. a million units.

In the sense of the present invention, endotoxin units (EU) are determined using the chromogenic-kinetic *Limulus* test introduced in 1997 in the BIA Code of Practice 9450 in the field of occupational safety. It is specified here as factor for the comparison between the concentration value in EU and ng that 10 EU=1 ng of endotoxin.

The *Limulus amoebocyte* lysate test (LAL test; first described by Bang 1956) is a sensitive and standardisable test for determining the endotoxin concentration. The LAL test makes use of the fact that the haemolymph of *Limulus polyphemus* (horseshoe crab) coagulates in the presence of endotoxin. A chemically pure standard lipopolysaccharide serves as comparison value. Reference is made to the European Pharmacopoeia for details in this regard (e.g. Eur. Ph. 5.0, 2.5.14 "*Bacterial Endotoxins*"). The test is preferably conducted in accordance with the standard conditions described therein.

It is most particularly preferred if the nuclease preparation according to the invention is free from endotoxins, i.e. no endotoxins are detectable with the above-described methods.

Since Gram-positive bacteria usually secrete secreted proteins directly into the medium (and not into the periplasm, for example), a step for lysis of the bacteria can possibly be omitted in the extraction of the nuclease.

In this case, the nuclease is preferably obtained directly from the medium. Various suitable methods for this are known to the person skilled in the art. These include, for example, methods based on centrifugation/separation operations, precipitation processes, chromatography processes and/or filtration processes.

Methods according to the invention that are characterized in that they do not comprise a step used for lysis of the bacteria are thus preferred.

The method according to the invention is preferably characterized in that the Gram-positive bacteria are removed from the medium by centrifugation and/or filtration.

Steps applied for lysis of bacteria include, for example, UV sonication, mechanical lysis such as e.g. lysis using a French press of a Manton-Gaulin homogeniser, osmotic lysis, chemical lysis such as e.g. by adding lysozyme and/or EDTA and/or triton and/or other detergents.

A further aspect of the invention relates to a composition containing a nuclease of a Gram-negative bacterium and a Gram-positive bacterium or their fragments or constituents or fragments thereof.

A further aspect of the invention relates to a method for the hydrolysis of DNA and/or RNA comprising the step of combining a nuclease or nuclease preparation according to the invention and the DNA and/or RNA to be hydrolysed under suitable conditions.

A further aspect of the invention relates to a Gram-positive bacterium containing
  a nuclease of a Gram-negative bacterium and/or
  a DNA sequence that encodes a nuclease of a Gram-negative bacterium.

A further aspect of the invention comprises the use of a nuclease and/or nuclease preparation obtainable via the method according to the invention for cleaving DNA and/or RNA.

In particular, the invention comprises the use of the nuclease and/or nuclease preparation obtainable via the method according to the invention for the production of products from the fields of pharmaceutics, cosmetics, diagnostics, food technology, biotechnology.

Products from the field of pharmaceutics include in particular chemical active substance molecules, biological active substances, in particular pharmacologically active biomolecules and pharmaceutical additives.

Biological active substances are, for example, antibodies, antibody fragments, proteins, peptides, genetically altered and/or inactivated viruses or virus particles and nucleic acids.

Products from the field of cosmetics include in particular proteins, peptides, biological active substances and cosmetic additives.

Products from the field of diagnostics include in particular proteins, peptides, enzymes, antibodies, antibody fragments, antigens, nucleic acids, enzyme substrates, cofactors and additives.

Products from the field of food technology include in particular proteins, enzymes, nutrients, food supplements, additives such as preservatives, dyes.

Products from the field of biotechnology include in particular proteins, enzymes and nucleic acids, chemicals and fine chemicals, synthesis building blocks for active substances.

EXAMPLES

The following illustrative examples serve to explain the invention in more detail, but are not to be interpreted as restrictive.

Illustrative Embodiment 1

Cloning of the Gene for the *Serratia marcescens* Nuclease into a Vacillus Expression Vector with a *Bacillus subtilis* Promoter Using two primers (SEQ-ID 173 and SEQ-ID 174) the gene of the *Serratia marcescens* nuclease including the signal peptide and a *Bacillus subtilis* ribosome binding site (SEQ-ID 175) from the synthetically created gene adapted to the codon usage of *Bacillus subtilis* is amplified by a PCR under the following conditions and the sequence (SEQ-ID 176) is obtained. On the amplified sequence the cut site for PaeI is located upstream of the nuclease gene and that for PstI downstream of the nuclease gene.

1.1 PCR:

| PCR batch: | 20 µl | 5 x Phusion polymerase buffer (Finnzymes) |
|---|---|---|
|  | 2 µl | dNTPs (per 10 mmol/liter) |
|  | 100 pmol | primer 1 (SEQ-ID 173) |
|  | 100 pmol | primer 2 (SEQ-ID 174) |
|  | 1 µl | original sequence (20 ng) |
|  | 1 U | Phusion polymerase (Finnzymes) |
|  | to 100 µl | dist. $H_2O$ |
| Temperature profile of the PCR: |  | 1 min/98° C. |
|  |  | 1. 10 sec/98° C. (denaturing) |
|  |  | 2. 20 sec/52° C. (addition) 30x |
|  |  | 3. 2 min 20 sec/72° C. (elongation) |
|  |  | 7 min/72° C. |

The resulting PCR products are purified by the High Pure PCR Product Purification Kit (Roche, Diagnostics GmbH, Mannheim) according to the manufacturer's specification.

1.2 Restriction Digest:

Any vector replicating in *Bacillus* species can be selected as expression vector. For preparation a promoter (SEQ-ID 171) with subsequent multiple cloning site (SEQ-ID 177) is inserted into this vector and any already present and interfering promoters and restriction cut sites removed, if necessary. Methods for producing such an empty expression vector are known to the person skilled in the art and are part of standard molecular biology.

To clone the gene into an appropriately prepared expression vector, the PCR product and the vector are incubated with the restriction endonucleases PaeI and PstI (all MBI Fermentas, Vilnius, Lithuania) as follows:

Restriction Digest Batches:

| PCR products: | | Vector: | |
|---|---|---|---|
| 2.4 µg | PCR product | 8 µg | vector |
| 5 µl | 10x Tango (MBI) | 4 µl | 10x Tango (MBI) |
| 30 U | PaeI | 20 U | PaeI |
| 10 U | PstI | 10 U | PstI |
| to 50 µl | dist. H₂O | to 40 µl | dist. H₂O |

The restriction digest batches are incubated for 2 h at 37° C. 1 U SAP (MBI Fermentas, Vilnius, Lithuania) is then added to the "vector batch" for dephosphorylation and incubated for a further 30 min at 37° C. A further 1 U SAP (MBI Fermentas, Vilnius, Lithuania) is then added and the mixture incubated for 30 min at 37° C. once again. The enzymes are then inactivated for 20 min at 80° C., extracted with phenol and chloroform and the batch precipitated with PEG for further concentration. The cut PCR product is purified by Promega Wizard SV Gel and PCR Clean-Up System (Promega GmbH, Mannheim).

1.3 Ligation, Transformation of *B. subtilis* and Plasmid Reisolation

The vector DNA and the PCR product are joined to one another by incubation with T4 DNA ligase as follows:

| Ligase batch: | 50 fmol | vector DNA |
|---|---|---|
| | 150 fmol | PCR product |
| | 2 µl | 10x Ligase Buffer (MBI) |
| | 1 µl | T4 DNA ligase |
| | to 20 µl | dist. H₂O |

The batches are incubated for 16 h at 16° C. and then the enzyme was inactivated by incubation for 10 minutes at 65° C. The batches are extracted with phenol and chloroform, precipitated with ethanol and taken up in 20 µl of deionised water. Before transforming 20 µl of 2×SMM are added to the batches. The batches are then used to transform *Bacillus subtilis* using the PEG protoblast method (Chang and Cohen, 1979). For isolation of the plasmids the High Pure Plasmid Isolation Kit (Roche, Diagnostics GmbH, Mannheim) is used according to manufacturers' specifications. The plasmids thus isolated are tested by sequencing the cloned gene with respect to its correct construction.

Illustrative Embodiment 2

Cloning of the Gene for the *Serratia marcescens* Nuclease into a *Bacillus* Expression Vector with a *Bacillus amyloliquefaciens* Promoter Using two primers (SEQ-ID 178 and SEQ-ID 179) the gene of the *Serratia marcescens* nuclease adapted to the codon usage of *Bacillus subtilis* including the signal peptide and a *Bacillus subtilis* ribosome binding site is amplified by a PCR and with the plasmid constructed under 1. as template under the following conditions. At the same time, cut sites for PaeI and Bpu1102I are contained on this PCR product (SEQ-ID 180).

2.1 PCR:

| PCR batch: | 20 µl | 5 x Phusion polymerase buffer (Finnzymes) |
|---|---|---|
| | 2 µl | dNTPs (per 10 mmol/liter) |
| | 200 pmol | primer 1 (SEQ-ID 178) |
| | 200 pmol | primer 2 (SEQ-ID 179) |
| | 1 µl | template vector from Example 1 (20 ng) |
| | 1 U | Phusion polymerase (Finnzymes) |
| | to 100 µl | dist. H₂O |

| Temperature profile of the PCR: | 1 min/98° C. |
|---|---|
| | 1. 10 sec/98° C. (denaturing) ⎫ |
| | 2. 20 sec/58° C. (addition)  ⎬ 30x |
| | 3. 2 min/72° C. (elongation) ⎭ |
| | 7 min/72° C. |

The resulting PCR products are purified by the High Pure PCR Product Purification Kit (Roche, Diagnostics GmbH, Mannheim) according to the manufacturer's specification.

2.2 Restriction Digest:

Any vector replicating in *Bacillus* species can be selected as expression vector. For preparation a promoter (SEQ-ID 172) with subsequent multiple cloning site (SEQ-ID 181) is inserted into this vector and any already present and interfering promoters and restriction cut sites removed, if necessary. Methods for producing such an empty expression vector are known to the person skilled in the art and are part of standard molecular biology.

To clone the gene into an appropriately prepared expression vector, the PCR product and the vector are incubated with the restriction endonucleases PaeI and Bpu1102I (all MBI Fermentas, Vilnius, Lithuania) as follows:

Restriction Digest Batches:

| PCR products: | | Vector: | |
|---|---|---|---|
| 1.5 µg | PCR product | 4 µg | vector |
| 5.5 µl | 10x Tango (MBI) | 5 µl | 10x Tango (MBI) |
| 20 U | PaeI | 20 U | PaeI |
| 10 U | Bpu1102I | 10 U | Bpu1102I |
| to 55 µl | dist. H₂O | to 50 µl | dist. H₂O |

The restriction digest batches are incubated for 2 h at 37° C. 1 U CIAP (MBI Fermentas, Vilnius, Lithuania) is then added to the "vector batch" for dephosphorylation and 5 µl of CIAP buffer 10× (MBI Fermentas, Vilnius, Lithuania) added thereto and incubated for a further 30 min at 37° C. A further 1 U CIAP (MBI Fermentas, Vilnius, Lithuania) is then added and the mixture incubated for 30 min at 37° C. once again. 5 mM of EDTA pH 8 are then added and the enzymes are inactivated for 30 min at 80° C. The cut PCR product is purified by Promega Wizard SV Gel and PCR Clean-Up System (Promega GmbH, Mannheim).

2.3 Ligation, Transformation of *B. subtilis* and Plasmid Reisolation

The vector DNA and the PCR product are joined to one another by incubation with T4 DNA ligase as follows:

| Ligase batch: | 50 fmol | vector DNA |
|---|---|---|
| | 150 fmol | PCR product |
| | 6 µl | 10x Ligase Buffer (MBI) |
| | 2 µl | T4 DNA ligase |
| | to 60 µl | dist. H₂O |

The batches are incubated for 16 h at 16° C. and then the enzyme was inactivated by incubation for 10 minutes at 65° C. The batches are extracted with phenol and chloroform, precipitated with ethanol and taken up in 20 µl of deionised water. Before transforming 20 µl of 2×SMM are added to the batches. The batches are then used to transform *Bacillus subtilis* using the PEG protoblast method (Chang and Cohen, 1979). For isolation of the plasmids the High Pure Plasmid Isolation Kit (Roche, Diagnostics GmbH, Mannheim) is used according to manufacturers' specifications.

Illustrative Embodiment 3

Cloning for Fusion of the Nuclease from *Serratia marcescens* with an AmyE Secretion Sequence Using two primers (SEQ-ID 174 and SEQ-ID 182) the gene of the *Serratia marcescens* nuclease adapted to the codon usage of *Bacillus subtilis* excluding the signal peptide is amplified by a PCR and with SEQ-ID 176 as template sequence under the following conditions.

3.1 PCR:
3.1.1. Nuclease PCR

| PCR batch: | 20 µl | 5 x Phusion polymerase buffer (Finnzymes) |
|---|---|---|
| | 2 µl | dNTPs (per 10 mmol/liter) |
| | 50 pmol | primer 1 (SEQ-ID 174) |
| | 50 pmol | primer 2 (SEQ-ID 182) |
| | 2 µl | template sequence (20 ng) |
| | 1 U | Phusion polymerase (Finnzymes) |
| | to 100 µl | dist. H$_2$O |
| Temperature profile of the PCR: | | 1 min/98° C. |
| | | 1. 10 sec/98° C. (denaturing) ⎫ |
| | | 2. 20 sec/53° C. (addition)    ⎬ 30x |
| | | 3. 2 min 15 sec/72° C. (elongation) ⎭ |
| | | 7 min/72° C. |

Using two primers (SEQ-ID 178 and SEQ-ID 183) the sequence encoding the secretion sequence of AmyE from *Bacillus subtilis* is amplified by PCR and the synthetically created sequence SEQ-ID 184 as template sequence under the following conditions.

3.1.2. AmyE Signal Sequence PCR

| PCR batch: | 20 µl | 5 x Phusion polymerase buffer (Finnzymes) |
|---|---|---|
| | 2 µl | dNTPs (per 10 mmol/liter) |
| | 50 pmol | primer 1 (SEQ-ID 178) |
| | 50 pmol | primer 2 (SEQ-ID 183) |
| | 2 µl | template sequence (20 ng) |
| | 1 U | Phusion polymerase (Finnzymes) |
| | to 100 µl | dist. H$_2$O |
| Temperature profile of the PCR: | | 1 min/98° C. |
| | | 1. 10 sec/98° C. (denaturing) ⎫ |
| | | 2. 20 sec/56° C. (addition)    ⎬ 30x |
| | | 3. 30 sec/72° C. (elongation) ⎭ |
| | | 7 min/72° C. |

The resulting PCR products are purified by the High Pure PCR Product Purification Kit (Roche, Diagnostics GmbH, Mannheim) according to the manufacturer's specification.

3.1.3. Fusion PCR AmyE Secretion Sequence with Nuclease from *Serratia marcescens*

| PCR batch: | 20 µl | 5 x Phusion polymerase buffer (Finnzymes) |
|---|---|---|
| | 2 µl | dNTPs (per 10 mmol/liter) |
| | 5.5 µl | PCR product 3.1.1 (600 fmol) |
| | 1 µl | PCR product 3.1.2 (600 fmol) |
| | 1 U | Phusion polymerase (Finnzymes) |
| | to 98 µl | dist. H$_2$O |
| Temperature profile of the PCR: | | 1 min/98° C. |
| | | 1. 10 sec/98° C. (denaturing) ⎫ |
| | | 2. 20 sec/72° C. (addition)    ⎬ 7x |
| | | 3. 2 min 15 sec/72° C. (elongation) ⎭ |

Directly after seven cycles elapsed 1 µl (100 pmol) in each case of primer 1 (SEQ-ID 178) and primer 2 (SEQ-ID 174) were added to the PCR batch and a further PCR was conducted with the following temperature profile:

| Temperature profile of the PCR: | 1 min/98° C. |
|---|---|
| | 1. 10 sec/98° C. (denaturing) ⎫ |
| | 2. 20 sec/53° C. (addition)    ⎬ 30x |
| | 3. 2 min 15 sec/72° C. (elongation) ⎭ |
| | 7 min/72° C. |

The resulting PCR products are purified by the High Pure PCR Product Purification Kit (Roche, Diagnostics GmbH, Mannheim) according to the manufacturer's specification and, as described under 1.2 and 1.3, were cloned into an expression vector that replicates in *Bacillus* species and carries a promoter with the following multiple cloning site (SEQ-ID 177).

Illustrative Embodiment 4

Cloning for Fusion of the Nuclease from *Serratia marcescens* with an AmyE Secretion Sequence and an N Terminal Affinity Tag (His-tag) on the Secreted Protein Using two primers (SEQ-ID 185 and SEQ-ID 179) the gene of the *Serratia marcescens* nuclease adapted to the codon usage of *Bacillus subtilis* excluding the signal peptide is amplified by PCR and the plasmid constructed under 3, as template under the following conditions.

4.1 PCR:
4.1.1. His-Nuclease PCR

| PCR batch: | 20 µl | 5 x Phusion polymerase buffer (Finnzymes) |
|---|---|---|
| | 20 µl | dNTPs (per 10 mmol/liter) |
| | 50 pmol | primer 1 (SEQ-ID 185) |
| | 50 pmol | primer 2 (SEQ-ID 179) |
| | 2 µl | template sequence (20 ng) |
| | 1 U | Phusion polymerase (Finnzymes) |
| | to 100 µl | dist. H$_2$O |
| Temperature profile of the PCR: | | 1 min/98° C. |
| | | 1. 10 sec/98° C. (denaturing) ⎫ |
| | | 2. 20 sec/57° C. (addition)    ⎬ 30x |
| | | 3. 2 min 10 sec/72° C. (elongation) ⎭ |
| | | 7 min/72° C. |

The resulting PCR products are purified by the High Pure PCR Product Purification Kit (Roche, Diagnostics GmbH, Mannheim) according to the manufacturer's specification.

4.1.2. Fusion PCR AmyE Signal Sequence with His-Tag and Nuclease from *Serratia marcescens*

| PCR batch: | 20 µl | 5 x Phusion polymerase buffer (Finnzymes) |
|---|---|---|
| | 2 µl | dNTPs (per 10 mmol/liter) |
| | 1.5 µl | PCR product 4.1.1 (600 fmol) |
| | 1 µl | PCR product 3.1.2 (600 fmol) |
| | 1 U | Phusion polymerase (Finnzymes) |
| | to 98 µl | dist. H$_2$O |
| Temperature profile of the PCR: | | 1 min/98° C. |
| | | 1. 10 sec/98° C. (denaturing) ⎫ |
| | | 2. 20 sec/72° C. (addition)    ⎬ 10x |
| | | 3. 2 min 30 sec/72° C. (elongation) ⎭ |

Directly after ten cycles elapsed 1 µl (100 pmol) in each case of primer 1 (SEQ-ID 178) and primer 2 (SEQ-ID 179) were added to the PCR batch and a further PCR was conducted with the following temperature profile:

| | |
|---|---|
| Temperature profile of the PCR: | 1 min/98° C.<br>1. 10 sec/98° C. (denaturing)<br>2. 20 sec/53° C. (addition)  ⎫<br>3. 2 min 15 sec/72° C. (elongation)  ⎬ 30x<br>7 min/72° C.  ⎭ |

The resulting PCR products are purified by the High Pure PCR Product Purification Kit (Roche, Diagnostics GmbH, Mannheim) according to the manufacturer's specification and, as described under 1.2 and 1.3, were cloned into an expression vector that replicates in Bacillus species and carries a promoter with the following multiple cloning site (SEQ-ID 177).

Illustrative Embodiment 5

Creation of the Expression Plasmids for Secretion of the Nuclease from Serratia marcescens The following plasmid constructs were constructed using molecular biological methods according to or in accordance with illustrative embodiments 1-4 and verified by sequencing:

1. Maltose-inducible promoter from B. subtilis+native nuclease (codon optimized), cf. illustrative embodiment 1
2. Maltose-inducible promoter from B. amyloliquefaciens+native nuclease including own signal sequence (codon optimized), cf. illustrative embodiment 2
3. Maltose-inducible promoter from B. subtilis+nuclease fused onto AmyE leader sequence (codon optimized), cf. illustrative embodiment 3
4. Maltose-inducible promoter from B. subtilis+native nuclease (codon optimized) including own signal sequence with C terminal His-tag (GGHHHHHHH) (SEQ ID NO. 186), analogous to illustrative embodiments 1 and 4
5. Maltose-inducible promoter from B. amyloliquefaciens+nuclease fused onto AmyE leader sequence (codon optimized), analogous to illustrative embodiments 2 and 3
6. Maltose-inducible promoter from B. subtilis+nuclease fused onto AmyE leader sequence (codon optimized) with N terminal His-tag (DHHHHHGG) (SEQ ID NO. 187), cf. Illustrative embodiment 4
7. Maltose-inducible promoter from B. amyloliquefaciens+nuclease fused onto AmyE leader sequence (codon optimized) with N terminal His-tag (DHHHHHGG) (SEQ ID NO. 187), analogous to illustrative embodiments 2 and 4
8. Growth phases induced npr promoter from B. amyloliquefaciens+nuclease fused onto AmyE leader sequence (codon optimized), analogous to illustrative embodiments 2 and 3

Illustrative Embodiment 6

Comparative Expression Tests with the Expression Constructs Created Under 5.

The plasmid constructs are tested for expression in B. subtilis wt168 trpC2 aprE nprE epr amyE bglC and also in B. amyloliquefaciens amy2 npr1 and amy 2 npr1 apr::ka.

a) Different liquid media are used therein for the expression
Medium 1:
LB medium (10 g/l trypton, 5 g/l yeast extract, 10 g/l NaCl, pH 7.0) with 5 µg/ml erythromycin+0.1% glucose;

For constructs with the maltose-inducible promoters the expression is induced by adding maltose (end concentration 1%) during transition to the stationary phase.
Medium 2:
5% maltose+0.1% glucose+2% soy peptone+2.5% Solulys 095E+0.5% $(NH_4)_2SO_4$+0.1% KCl+0.05% $Mg_2SO_4.7H_2O$
Medium 3:
10% maltose+0.1% glucose+2% soy peptone+2.5% Solulys 095E+0.5% $(NH_4)_2SO_4$+0.1% KCl+0.05% $Mg_2SO_4.7H_2O$
Medium 4:
100 mM tris-HCl pH 7.5+10% maltose+0.1% glucose+2% soy peptone+2.5% Solulys 095E+0.5% $(NH_4)_2SO_4$+0.1% KCl+0.05% $Mg_2SO_4.7H_2O$ b) For the cultivation of precultures LB medium is used with 2% glucose and 5 µg/ml of erythromycin.

c) For strain retention (glycerol stock) LB medium is used with 2% glucose and 5 µg/ml of erythromycin. The medium is inoculated with a single colony from the plate. The cultures are incubated in culture tubes overnight at 30° C. with agitation (200 rpm). The next morning 200 µl of 60% sterile glycerine is added to 600 µl of culture. The batches were mixed and frozen in liquid nitrogen. Storage took place at −80° C.

d) For propagating the strains on plates LB medium is used with 5 µg/ml of erythromycin+2% glucose+1.5% agar.

e) For detecting nuclease-positive colonies on the plate LB medium is used with 5 µg/ml of erythromycin+0.1% glucose+1% maltose+0.2% herring sperm DNA (AppliChem A2160)+0.2% RNA from yeast (Roche 109223) (for activity)+1.5% agar. Nuclease-positive colonies are made visible by flooding the plate with 1N HCl after 2 days of incubation. In this case, positive candidates are surrounded by a clear halo.

f) For expression tests the cultures are incubated at 37° C. Liquid cultures are agitated horizontally at 150 rpm in this case. Precultures are incubated overnight at 30° C.

g) Expression tests
i. Medium 1 Bacillus subtilis or Bacillus amyloliquefaciens with plasmid constructs 1-7
Working from a preculture 100 ml of medium 1 are inoculated with 1 ml of preculture. The growth curve is determined and when the culture enters the stationary phase 2 ml of 50% maltose (end concentration 1%) are added to medium 2. The culture is incubated still with agitation overnight at 37° C. The next morning the nuclease activity is determined in the supernatant.
ii. Medium 1 Bacillus subtilis or Bacillus amyloliquefaciens with plasmid construct 8
Working from a preculture 100 ml of medium 1 are inoculated with 1 ml of preculture. The culture is incubated for 24 hours with agitation at 37° C. The next morning the nuclease activity is determined in the supernatant.
iii. Media 2, 3, 4 Bacillus subtilis or Bacillus amyloliquefaciens with plasmid constructs 1-8
Working from a preculture 100 ml of medium 1 are inoculated with 1 ml of preculture. The culture is incubated over a week still with agitation at 37° C. The nuclease activity is determined in the supernatant every day.

h) Nuclease activity measurements
Chemicals
DNA (salmon testes)—Sigma D1626→for assay
RNA (yeast) Roche 109223→for plates
DNA (salmon sperm) AppliChem A2160→for plates
BSA (10 mg/ml) NEB B9001S Buffer, Solutions
1 M tris-HCl pH 8.2; autoclave
10 mM MgCl$_2$; autoclave
assay buffer (always produce fresh)

| Example for 100 ml | | |
|---|---|---|
| | End concentration | Stock solution |
| tris HCl | 50 mM | 5 ml |
| BSA | 0.1 mg/ml | 1 ml |
| MgCl$_2$ | 1 mM | 1 ml |

Fill to 100 ml with sterile dist. water substrate buffer (1 mg/ml of DNA Sigma D1626 in assay buffer)
4% perchloric acid (slowly add 10 ml of 70% perchloric acid to 165 ml of water)
100 µl of substrate are mixed with 20 µl of solution containing DNase. If a dilution of the DNase is necessary, then the enzyme is diluted in assay buffer. The mixture must be diluted to different degrees, depending on activity and purity. The *S. marescens* nuclease is replaced by assay buffer as blank reading value.

The solution is incubated for exactly 20 minutes at 37° C. and the reaction is then stopped by adding 100 µl of 4% perchloric acid. The solution is then immediately incubated on ice for 10 minutes to assure a complete precipitation of the unconverted DNA. The precipitated DNA is then centrifuged off (16 000×g; 10 min; 4° C.). 150 µl is removed from the supernatant and is measured diluted 1:5 with water. For this, the 150 µl of supernatant is mixed with 600 µl of water and the extinction is measured in a quartz cuvette photometer at 260 nm, which had previously been adjusted with water. In this case, a unit corresponds to the amount of enzyme that causes an absorption change at 260 nm of 1 in 60 minutes.

i) *S. marescens* nuclease expression rates obtained (MU per liter of supernatant):

| Medium | 1 | 2 | 3 | 4 |
|---|---|---|---|---|
| *B. subtilis* aprE nprE epr amyE bglC with plasmid construct 1 | 0.4 | | | |
| *B. subtilis* aprE nprE epr amyE bglC with plasmid construct 2 | 0.6 | | | |
| *B. subtilis* aprE nprE epr amyE bglC with plasmid construct 3 | 2.5 | | | |
| *B. subtilis* aprE nprE epr amyE bglC with plasmid construct 4 | 0.2 | | | |
| *B. subtilis* aprE nprE epr amyE bglC with plasmid construct 5 | 3.7 | 0.7 | | |
| *B. subtilis* aprE nprE epr amyE bglC with plasmid construct 6 | 1.6 | | | |
| *B. subtilis* aprE nprE epr amyE bglC with plasmid construct 8 | 1.0 | 0.3 | | |
| *B. amyloliquefaciens* amy2 nprl with plasmid construct 1 | 0.9 | | | |
| *B. amyloliquefaciens* amy2 nprl with plasmid construct 2 | 1.1 | | | |
| *B. amyloliquefaciens* amy2 nprl with plasmid construct 3 | 0.5 | | | |
| *B. amyloliquefaciens* amy2 nprl with plasmid construct 5 | 1.3 | 25.7 | 15.1 | 26.4 |
| *B. amyloliquefaciens* amy2 nprl with plasmid construct 8 | 1.0 | 12.1 | | |
| *B. amyloliquefaciens* amy2 nprl apr::kan with plasmid construct 5 | | | 21.1 | 27.7 |
| *B. amyloliquefaciens* amy2 nprl apr::kan with plasmid construct 6 | | | | 10.6 |
| *B. amyloliquefaciens* amy2 nprl apr::kan with plasmid construct 7 | | | | 11.9 |

Illustrative Embodiment 7

Heterologous Expression of the *Serratia marcescens* Nuclease in *Escherichia coli*.

Cloning and Expression

Expression vectors were constructed by insertion of an open DNA fragment into the plasmid pBR327 (DSMZ, Braunschweig). The DNA fragment comprised the open reading frame of the *Serratia marcescens* nuclease including its native signal sequence under the control of the native *Serratia marcescens* nuclease promoter. Two variants were constructed, which differ in orientation of the DNA fragment with respect to the resistance gene of pBR327. The expression of the nuclease occurs in the *E. coli* strain MC1000 (from CGSC, New Haven USA) in the agitation vessel in LB medium with 0.2% glucose and 100 µg/ml of ampicillin at 37° C. for 72 h. The strain MC1000 with the empty plasmid pBR327 was used as control. Samples of the cultures were taken at different times. The cells were separated by centrifugation and the nuclease activity was determined in the supernatant. The determination of the expressed enzyme activities occurs as described under h) in illustrative embodiment 6. The following maximum expression yields were obtained:

| | MU per liter of culture supernatant |
|---|---|
| MC1000 pBR327 | 0.042 |
| MC1000 pBR327 + nuclease variant 1 | 0.066 |
| MC1000 pBR327 + nuclease variant 2 | 0.074 |

In a second batch the *Serratia marcescens* nuclease was expressed in the fermenter. LB medium with 0.2% glucose and 100 µg/ml of ampicillin was used as medium. The growth temperature amounted to 35° C. The pH value was set at 8.4. Ventilation occurred at 500 rpm with 1 vvm of air. Fermentation occurred for 72 h. Samples of the cultures were taken at different times. The cells were separated by centrifugation and the nuclease activity was determined in the supernatant.

The content of nuclease activity in the periplasm of the strains was also examined. For this, the separated pellet of the cells was taken up in 0.03 M tris-HCl pH 8 20% saccharose. 80 ml of buffer was used for 1 g of pellet EDTA (end concentration 1 mM) was then added to the suspension. The suspension was incubated for 10 minutes with agitation. The cells were then pelletised by centrifugation. The pellets were taken up in a sample volume of cold deionised water with a temperature of 4° C. and incubated at 4° C. for 10 minutes. The suspension was centrifuged and the nuclease activity measured in the supernatant.

The determination of the expressed enzyme activities occurs as described under h) in illustrative embodiment 6. The following maximum expression yields were obtained:

|  | MU per liter of culture supernatant | MU per liter of culture periplasm |
| --- | --- | --- |
| MC1000 pBR327 | 0.032 | 0.002 |
| MC1000 pBR327 + nuclease variant 1 | 0.062 | 0.023 |
| MC1000 pBR327 + nuclease variant 2 | 0.086 | 0.025 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A method for producing a *Serratia marcescens* nuclease comprising:
   culturing a *Bacillus subtilis* bacterium or a *Bacillus amyloliquefaciens* bacterium comprising a nucleic acid with a nucleotide sequence encoding the *Serratia marcescens* nuclease in a culture medium to express said nucleic acid to secrete the nuclease,
   wherein the *Serratia marcescens* nuclease is fused to a *Bacillus subtilis* or *Bacillus amyloliquefaciens* AmyE secretion signal,
   wherein the nucleic acid comprises a *Bacillus subtilis* or a *Bacillus amyloliquefaciens* maltose-inducible promoter and expression of the *Serratia marcescens* nuclease is controlled by the maltose-inducible promoter, and
   wherein the method achieves a yield of the secreted nuclease of at least 5,000 nuclease units per mL of culture medium.

2. The method according to claim 1, wherein said nucleic acid is integrated into the chromosome of the *Bacillus subtilis* bacterium or the *Bacillus amyloliquefaciens* bacterium.

3. The method according to claim 1, wherein the *Bacillus subtilis* bacterium or the *Bacillus amyloliquefaciens* bacterium is a low-protease *Bacillus subtilis* bacterium or *Bacillus amyloliquefaciens* bacterium.

4. The method according to claim 1, wherein the *Serratia marcescens* nuclease is fused to an affinity tag.

5. The method according to claim 1, wherein said nucleic acid is within an expression vector.

6. The method according to claim 1, excluding any purification step for removing endotoxins.

7. The method according to claim 1, wherein the bacterium is *Bacillus subtilis* and the secretion signal is *Bacillus subtilis* AmyE secretion signal.

8. The method according to claim 7, wherein said nucleic acid is integrated into the chromosome of the *Bacillus subtilis* bacterium.

9. The method according to claim 1, wherein the bacterium is *Bacillus* amyloliquefaciens and the secretion signal is *Bacillus subtilis* AmyE secretion signal.

10. The method according to claim 9, wherein said nucleic acid is integrated into the chromosome of the *Bacillus amyloliquefaciens* bacterium.

11. The method according to claim 1, wherein the bacterium is *Bacillus amyloliquefaciens*, the secretion signal is *Bacillus subtilis* AmyE secretion signal, and the nucleic acid comprises a *Bacillus amyloliquefaciens* maltose-inducible promoter.

12. The method of claim 1, wherein the *Bacillus subtilis* or the *Bacillus amyloliquefaciens* bacterium is cultured in a medium comprising 1% maltose.

13. The method of claim 1, wherein the *Bacillus subtilis* or the *Bacillus amyloliquefaciens* bacterium is cultured in a medium comprising 5% maltose.

14. The method of claim 1, wherein the *Bacillus subtilis* or the *Bacillus amyloliquefaciens* bacterium is cultured in a medium comprising 10% maltose.

15. A method for producing a *Serratia marcescens* nuclease comprising:
   culturing a *Bacillus amyloliquefaciens* bacterium comprising a nucleic acid with a nucleotide sequence encoding the *Serratia marcescens* nuclease in a culture medium to express said nucleic acid to secrete the nuclease,
   wherein the *Serratia marcescens* nuclease is fused to a *Bacillus subtilis* AmyE secretion signal,
   wherein the nucleic acid comprises a *Bacillus amyloliquefaciens* neutral protease (npr) promoter and expression of the *Serratia marcescens* nuclease is controlled by the npr promoter; and
   wherein the method achieves a yield of the secreted nuclease of at least 5,000 nuclease units per mL of culture medium.

16. The method of claim 15, wherein the *Bacillus amyloliquefaciens* bacterium is cultured in a medium comprising 1% or 10% maltose.

17. The method of claim 15, wherein the *Bacillus amyloliquefaciens* bacterium is cultured in a medium comprising 5% maltose.

18. The method according to claim 1, wherein the bacterium is *Bacillus subtilis*, the secretion signal is *Bacillus subtilis* AmyE secretion signal, and the nucleic acid comprises a *Bacillus subtilis* maltose-inducible promoter.

19. The method according to claim 1, wherein the amino acid sequence of the *Serratia marcescens* nuclease is SEQ ID NO: 3.

20. The method according to claim 7, wherein the amino acid sequence of the *Serratia marcescens* nuclease is SEQ ID NO: 3.

21. The method according to claim 9, wherein the amino acid sequence of the *Serratia marcescens* nuclease is SEQ ID NO: 3.

22. The method according to claim 11, wherein the amino acid sequence of the *Serratia marcescens* nuclease is SEQ ID NO: 3.

23. The method according to claim 15, wherein the amino acid sequence of the *Serratia marcescens* nuclease is SEQ ID NO: 3.

24. The method according to claim 18, wherein the amino acid sequence of the *Serratia marcescens* nuclease is SEQ ID NO: 3.

* * * * *